(12) United States Patent
Bishop et al.

(10) Patent No.: US 6,316,462 B1
(45) Date of Patent: Nov. 13, 2001

(54) METHODS OF INDUCING CANCER CELL DEATH AND TUMOR REGRESSION

(75) Inventors: Walter R. Bishop, Pompton Plains; Diana L. Brassard, Union; Tattanahalli L. Nagabhushan, Parsippany, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/289,255

(22) Filed: Apr. 9, 1999

(51) Int. Cl.[7] .................... C07D 471/00; C07D 315/00; A61K 31/44
(52) U.S. Cl. .................... 514/290; 549/425; 546/80
(58) Field of Search ................. 546/80; 549/425; 514/290

(56) References Cited

U.S. PATENT DOCUMENTS

| | | |
|---|---|---|
| 4,764,378 | 8/1988 | Keith et al. .................... 424/435 |
| 4,826,853 | 5/1989 | Piwinski et al. .................... 514/290 |

(List continued on next page.)

FOREIGN PATENT DOCUMENTS

| | | |
|---|---|---|
| 0 214 092 | 3/1987 | (EP) . |
| 0 270 818 | 6/1988 | (EP) . |
| 0 341 860 | 11/1989 | (EP) . |
| 0 396 083 | 11/1990 | (EP) . |
| 0 856 315 A1 | 5/1998 | (EP) . |
| 1 560 406 | 2/1980 | (GB) . |
| 0 495 484 | 7/1992 | (WO) . |
| WO 92/11034 | 7/1992 | (WO) . |
| WO 95/10515 | 4/1995 | (WO) . |
| WO 95/10516 | 4/1995 | (WO) . |
| WO 95/15949 | 6/1995 | (WO) . |
| WO 96/30018 | 10/1996 | (WO) . |
| WO 96/30362 | 10/1996 | (WO) . |
| WO 96/30363 | 10/1996 | (WO) . |
| WO 96/31477 | 10/1996 | (WO) . |
| WO 96/31478 | 10/1996 | (WO) . |
| WO 97/23478 | 7/1997 | (WO) . |
| WO 97/36587 | 10/1997 | (WO) . |
| WO 97/38664 | 10/1997 | (WO) . |
| WO 97/38697 | 10/1997 | (WO) . |
| WO 97/45412 | * 12/1997 | (WO) . |
| WO 97/545412 | 12/1997 | (WO) . |

(List continued on next page.)

OTHER PUBLICATIONS

Gibbs, J. B., *Cell*, 65: 1–4, 1991.
Sepp–Lorenzino, et al., *Cancer Research*, 55: 5302–5309, 1995.
Alexander Levitzki and Aviv Gazit, *Science*, 267: 1782–1787, 1995.

(List continued on next page.)

*Primary Examiner*—Ralph Gitomer
*Assistant Examiner*—Devesh Khare
(74) *Attorney, Agent, or Firm*—James M. Gould; Allan N. Kutzenco

(57) ABSTRACT

Methods are provided for treating cancer, comprising administering (1) a farnesyl protein transferase inhibitor in conjunction with (2) an additional Ras signaling pathway inhibitor to induce cancer cell death and tumor regression.

55 Claims, 7 Drawing Sheets

U.S. PATENT DOCUMENTS

| | | | |
|---|---|---|---|
| 5,073,379 | 12/1991 | Klimesch et al. | 424/467 |
| 5,089,496 | 2/1992 | Piwinski et al. | 514/253 |
| 5,151,423 | 9/1992 | Piwinski et al. | 514/254 |
| 5,393,890 | 2/1995 | Syoji et al. | 546/80 |
| 5,416,091 | 5/1995 | King | 514/290 |
| 5,464,840 | 11/1995 | Ting et al. | 514/277 |
| 5,512,293 | 4/1996 | Landrau et al. | 424/449 |
| 5,523,095 | 6/1996 | Wilson et al. | 424/486 |
| 5,561,117 | 10/1996 | Wong et al. | 514/291 |
| 5,595,762 | 1/1997 | Derrieu et al. | 424/490 |
| 5,661,152 | 8/1997 | Bishop et al. | 514/254 |
| 5,672,611 | 9/1997 | Doll et al. | 514/325 |
| 5,677,171 | 10/1997 | Hudziak et al. | 435/240.27 |
| 5,684,013 | 11/1997 | Afonso et al. | 514/290 |
| 5,696,121 | 12/1997 | Bishop et al. | 514/254 |
| 5,700,806 | 12/1997 | Doll et al. | 514/290 |
| 5,703,090 | 12/1997 | Afonso et al. | 514/290 |
| 5,712,280 | 1/1998 | Doll et al. | 514/253 |
| 5,714,609 | 2/1998 | Bishop et al. | 546/93 |
| 5,719,148 | 2/1998 | Bishop et al. | 514/228.2 |
| 5,721,236 | 2/1998 | Bishop et al. | 514/255 |
| 5,728,703 | 3/1998 | Bishop et al. | 514/254 |
| 5,807,853 | 9/1998 | Bishop et al. | 514/228.2 |
| 5,852,034 | 12/1998 | Njoroge et al. | 514/290 |
| 5,858,411 | 1/1999 | Nakagami et al. | 424/489 |
| 5,861,395 | 1/1999 | Taveras et al. | 514/232.8 |
| 5,874,442 | 2/1999 | Doll et al. | 514/790 |
| 5,877,177 | 3/1999 | Taveras | 514/254 |
| 5,925,639 | 7/1999 | Doll et al. | 514/254 |
| 5,939,416 | 8/1999 | Rane et al. | 514/228.8 |
| 5,945,429 | 8/1999 | Taveras et al. | 514/290 |
| 5,958,890 | 9/1999 | Rane et al. | 514/43 |
| 5,958,939 | 9/1999 | Afonso et al. | 514/290 |
| 5,958,940 | 9/1999 | Rane et al. | 514/290 |
| 5,965,570 | 10/1999 | Cooper et al. | 514/290 |
| 5,972,381 | 10/1999 | Sangekar et al. | 424/451 |
| 5,985,879 | 11/1999 | Taveras et al. | 514/254 |
| 6,030,982 | 2/2000 | Njoroge et al. | 514/290 |
| 6,040,305 | 3/2000 | Taveras | 514/232.8 |
| 6,071,907 | 6/2000 | Njoroge et al. | 514/278.2 |

FOREIGN PATENT DOCUMENTS

| | | |
|---|---|---|
| WO 98/00113 | 1/1998 | (WO) . |
| WO 98/11091 | 3/1998 | (WO) . |
| WO 98/35554 | 8/1998 | (WO) . |
| WO 98/54966 | 10/1998 | (WO) . |
| WO 99/31140 | 6/1999 | (WO) . |
| WO 99/32118 | 7/1999 | (WO) . |

OTHER PUBLICATIONS

Gorczyca, et al., *Cancer Research*, 53: 1945–1951, 1993.
Liu, et al., *Cancer Research*, 58: 4947–4956, 1998.
Lowy, D. R. and Willumsen, B.M., *Annu. Rev. Biochem*, 62: 851–91, 1993.
Mendelsohn, J., *J. National Cancer Inst.*, 13: 125–131, 1992.
Moasser, M. M., *Proc. Natl. Acad. Sci. USA*, 95: 1369–1374, 1998.
Graham, S. L., *Exp. Opin. Ther. Patents*, 5(12): 1269–1285, 1995.
Gutkind, J. S., *J Biol Chem.*, 273: 1839–1842, 1998.
Heldin, C.H., *Cell*, 80: 213–223, 1995.
Wen–Chun Hung and Lea–Yea Chaung, *Int. J. Oncology*, 12: 137–140, 1998.
James, G. L., *J. Biol. Chem.*, 269: 27705–27714, 1994.
Kohl, et al., *Nature Medicine*, 1: 792–797, 1995.
Kovalenko, M., et al., *Cancer Research*, 54: 6106–6114, 1994.
Lebowitz, P.F., et al., *J. Biol. Chem.*, 272: 15591–15594, 1997.
Meg Trahey and Frank McCormick, *Science*, 238: 542–545, 1987.
Wang, H., et al., *Anticancer Research*, 18: 2297–2300, 1998.
Whyte, D. B., et al., *J. Biol. Chem.*, 272: 14459–14464, 1997.
Zhang, F. L., et al., *J. Biol. Chem.*, 272: 10232–10239, 1937.
Deborah K. Morrison and Richard E. Cutler, Jr., *Curr Opin Cell Biol.*, 9: 174–179, 1997.
Moyer, J. D., et al., *Cancer Research*, 57: 4838–4848, 1997.
Norgaard, P., et al., *Clin. Cancer Res.*, 5: 35–42, 1999.
Pegram, M. D., et al., *J. Clin Oncol.*, 16: 2659–2671, 1998.
Raff, Martin, *Nature*, 396: 119–122, 1998.
Resnicoff, Mariana, *Int. J. Mol. Med.*, 1: 883–888, 1998.
Suzuki, N., et al., *Proc. Natl. Acad. Sci USA*, 95: 15356–15361, 1998.
Nancy A. Thornberry and Yuri Lazebnik, *Science*, 281: 1312–1316, 1998.
Alessi, D.R., et al., *J Biol Chem*, 270: 27489–27494, 1995.
Goldstein, N. I., *Clin. Cancer Res.*, 1: 1311–1318, 1995.
Barrington, R. E., et al., *Mol. Cell. Biol.*, 18: 85–92, 1998.
Bishop, W.R., et al., *J. Biol. Chem.*, 270: 30611–30618, 1995.
Campbell, S. L., et al., *Oncogene*, 17: 1395–1413, 1998.
Dengler, W. A., et al., *Anti–Cancer Drugs*, 6: 522–532, 1995.
Brian C. Duckworth and Lewis C. Cantley, *J. Biol. Chem.*, 272: 27665–27670, 1997.
Dudley, D. T., *Proc. Natl., Acad. Sci. USA*, 92: 7686–7689, 1995.
Favata, M. F., *J. Biol. Chem.*, 273: 18623–18632, 1998.
Fry, D. W., *Science*, 265: 1093–1095, 1994.
Du, W., et al., *Cancer Research*, 59: 4208–4212, 1999.
Levitzki et al., XP002048355, *Science US*, vol. 267, pp. 1782–1788 (1995).
Graham et al., XP000881449, *Patent Update Oncologic, Endocrine & Metabolic Inhibitors of Protein Farnesylation*, vol. 6, No. 12, pp. 1295–1394 (1996).
Njoroge et al., *Bioorganic & Medicinal Chemistry Letters*, vol. 6, No. 24, pp. 2977–2982 (1996).
Buhler, et al., *Polyvinylpyrrolidone for the Pharm. Industry*, $2^{nd}$ Edition, pp. 88–105; 169–177; 245–271 (1993).
Florence et al. XP00296892, *Physicochemical Principles of Pharmacy*, MacMillan Press Ltd., Chapter 2.9, pp. 41–45 (1988).
*Patent Abstracts of Japan*, vol. 096, No. 006 (1996).

* cited by examiner

METHODS OF INDUCING CANCER CELL DEATH AND TUMOR REGRESSION

FIELD OF THE INVENTION

This invention describes novel methods of treating subjects afflicted with cancers, including tumors and metastatic disease. In particular, this invention provides methods of treating cancer comprising the combined use of (1) a farnesyl protein transferase ("FPT") inhibitor and (2) an additional Ras signaling pathway inhibitor to induce a synergistic level of cancer cell death (apoptotic cell death in particular), thus permitting low dose treatment regimens.

BACKGROUND OF THE INVENTION

FIG. 1 of the present specification shows a simplified linear depiction of a signal transduction pathway that leads to cellular proliferation. This pathway is referred to herein as the "Ras signaling pathway" because Ras is a central relay in this pathway, receiving signals from upstream elements (e.g., growth factor receptors) and transmitting them to downstream elements.

The signaling pathways initiated by growth factor receptors which lead to cellular proliferation, and in some cases malignant transformation, are being elucidated. Many growth factor receptors such as those for epidermal growth factor (EGF) and platelet-derived growth factor (PDGF), as well as EGF receptor-related molecules (e.g. Her-2/Neu/ErbB2), possess an intrinsic tyrosine kinase activity which is activated by ligand-induced receptor dimerization (Heldin, 1995). This results in autophosphorylation of the receptor on tyrosine residues and the binding of proteins containing Src-homology 2 (SH2) domains. Two such SH2 proteins are Grb2 and SHC which indirectly activate the plasma membrane-associated, small GTP-binding protein Ras. Ras activation also occurs in response to ligand binding to seven transmembrane domain G-protein coupled receptors (e.g. Gutkind, 1998). Activation of Ras and other growth factor receptor-regulated signaling pathways ultimately leads to changes in the cytoskeleton and gene expression which are necessary for cellular proliferation, differentiation, and transformation (reviewed in Campbell et al., 1998).

The 3 human ras genes (Ha-Ras, N-Ras, and Ki-Ras) encode 4 proteins (due to alternative splicing of the Ki-Ras mRNA). Under normal circumstances, Ras proteins cycle between an active (GTP-bound) state and an inactive (GDP-bound) state. Ras activation occurs by exchange of bound GDP for GTP, which is facilitated by a family of guanine nucleotide exchange factors. Ras inactivation occurs by hydrolysis of bound GTP to GDP. This reaction is facilitated by GTPase activating proteins (GAPs) (Trahey and McCormick, 1987). In many human cancers, Ras proteins become oncogenically activated by mutations which destroy their GTPase activity, and thus deregulate Ras signaling (reviewed in Campbell et al., 1998).

Multiple candidate Ras effectors exist that may serve downstream of Ras in signal transduction and oncogenic transformation, including members of the Rho family of small GTPases, phosphatidylinositol-3 kinase (PI3K) and the serine/threonine protein kinase c-Raf-1 (reviewed in Campbell et al., 1998). Raf-mediated signaling is the best characterized Ras effector pathway. Activated Ras recruits Raf to the membrane where Raf activation occurs. Activated Raf is the initial component of a kinase cascade, the Mitogen-Activated Protein Kinase (MAPK) cascade (reviewed in Lowy and Willumsen, 1993; Campbell et al., 1998). Raf phosphorylates and activates the MEKI and MEK2 (MAPK/ERK kinase) protein kinases which, in turn, phosphorylate and activate the Extracellular signal Regulated Kinases ERK1 and ERK2 (also known as MAPK1 and MAPK2). Unlike their downstream targets, ERK1,2, the MEK1,2 proteins are highly specific enzymes whose only known substrates are the ERK1,2 proteins. Upon activation, ERK1 and ERK2 phosphorylate (and thus regulate) a variety of target proteins, including nuclear transcription factors, leading to the ultimate cellular response. This linear pathway of Ras signaling is diagrammed in FIG. 1.

The importance of these signaling pathways in the abnormal growth of cancer cells is indicated by the finding that growth factor receptor and Ras pathway components are often mutated and/or overexpressed in cancer. For example, Ras is mutationally activated in about 30% of human cancers including a high percentage of major epithelial cancers such as lung, colon and pancreatic cancers. Additionally, overexpression of growth factor receptors occurs in a number of cancers (e.g. overexpression of the Her-2/Neu receptor occurs in about 30% of human breast cancer). These observations have led to the pursuit and development of agents designed to block individual components of either signal transduction pathway. While such agents hold potential as novel cancer therapeutics, many inhibitors of signal transduction are thought to act in a cytostatic rather than a cytotoxic fashion by blocking the cell's progression through the cell cycle. This distinguishes them from traditional cancer chemotherapy drugs in being less toxic but also possessing less dramatic antitumor activity.

Therefore, there remains a challenge to provide new and improved methods of treating cancer. For instance, to treat tumorigenic cancer cells, it would be highly desirable to provide new methods that achieve a dramatic and selective induction of cancer cell death while minimizing potential toxic side effects against normal, untransformed cells. The present invention provides just such methods of treatment.

SUMMARY OF THE INVENTION

The present invention provides methods of treating cancer in a patient (e.g., a mammal such as a human) in need of such treatment, comprising administering an effective amount of (1) a farnesyl protein transferase (FPT) inhibitor and (2) an additional Ras signaling pathway inhibitor. The methods of the present invention achieve an unexpectedly dramatic induction of cancer cell death (apoptotic cell death in particular). The effects are synergistic, and highly selective against transformed cells (particularly tumorigenic cancer cells), thus enabling the use of low doses to minimize potential toxic side effects against normal, untransformed cells. Moreover, the methods of the present invention were surprisingly found to have a long-lasting, sustained effect on blocking cell signaling, again while minimizing potential toxic side effects against normal, untransformed cells. None of these effects, let alone their magnitude, could have been predicted prior to the present invention. Furthermore, taking advantage of the surprising synergy and sustained, long-lasting effects of this invention, special low-dose methods are provided so that cancer cell death is effectively achieved while, at the same time, maintaining low risk of potential toxic side effects on normal, untransformed cells. The methods of the present invention are particularly useful for the treatment of various tumorigenic cancers, especially epithelial cancers, (e.g., pancreatic cancer, ovarian cancer, prostate cancer, lung cancer, breast cancer, colorectal cancer, and bladder cancer), and melanoma.

BRIEF DESCRIPTION OF THE DRAWINGS

The FPT Inhibitory Compound referred to in FIGS. 1 through 7 (sometimes referred to as "SCH 66336") is as follows:

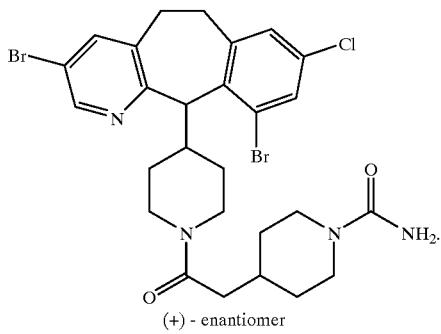

(+) - enantiomer

Figure 1:
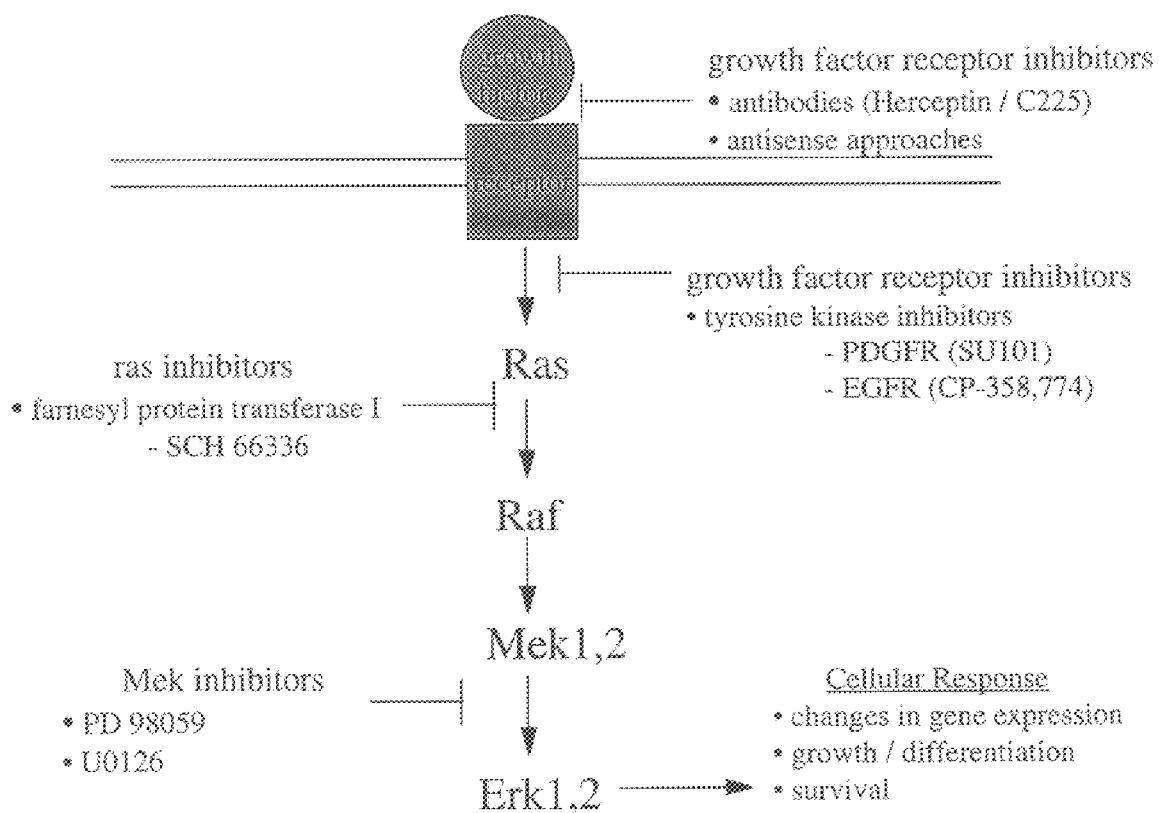

FIG. 1: Ras Signal Transduction: Schematic representation of the components of the Ras/MAPK signal transduction pathway. This linear pathway from growth factor receptor to ERK activation was the first Ras-mediated pathway to be elucidated. Also indicated are steps targeted by various inhibitors including the FPT inhibitor SCH 66336 and the MEK inhibitors PD098059 and U0126.

Figure 2:
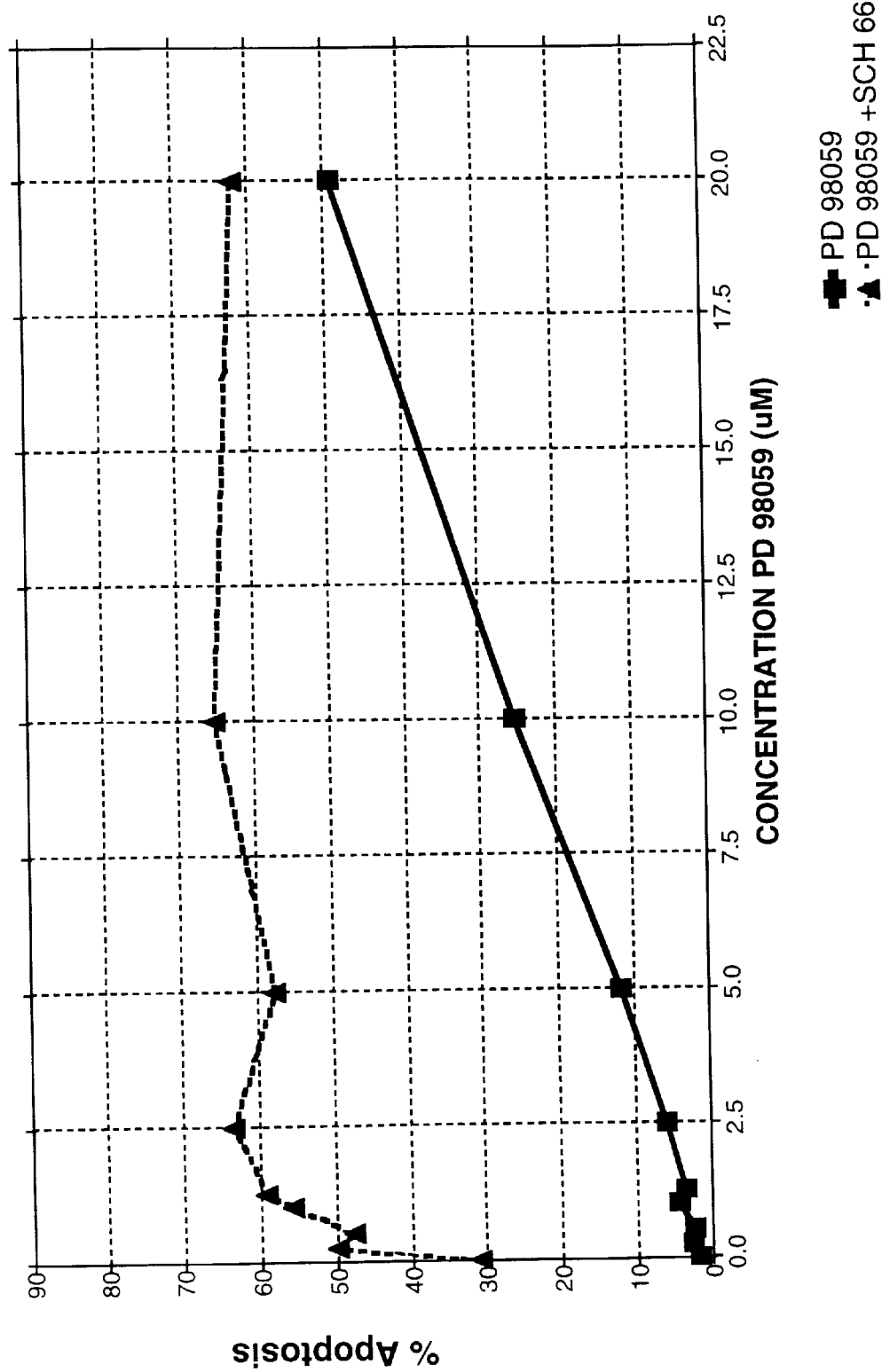

FIG. 2: The dose-dependent apoptotic response to treatment with PD098059 is enhanced by addition of SCH 66336: H-Ras-CVLS-transformed Rat2 cells were treated for 36 hours with the indicated concentrations of PD098059 (A385-023-M005; Alexis Corporation), either alone or in a combination with SCH 66336. The cells were harvested by trypsin/EDTA treatment, fixed in Acetone/Methanol (50%:50%) at −20° C. for 30 min, extensively washed with PBS, and labeled for 30 min at room temperature with PBS containing 75 µg/ml propidium iodide (PI; Calbiochem; La Jolla, Calif.), and 500 µg/ml RNase (Sigma; St. Louis, Mo.). Apoptosis was measured by propidium iodide staining of chromosomal DNA with FACS analysis of the cell population (FACS-Calibur, Becton-Dickinson; Mountain View, Calif.). The concentration of PD098059 was varied from 0.25 to 20 µM in the presence (▲) or absence (■) of 100 nM SCH 66336.

Figure 3:
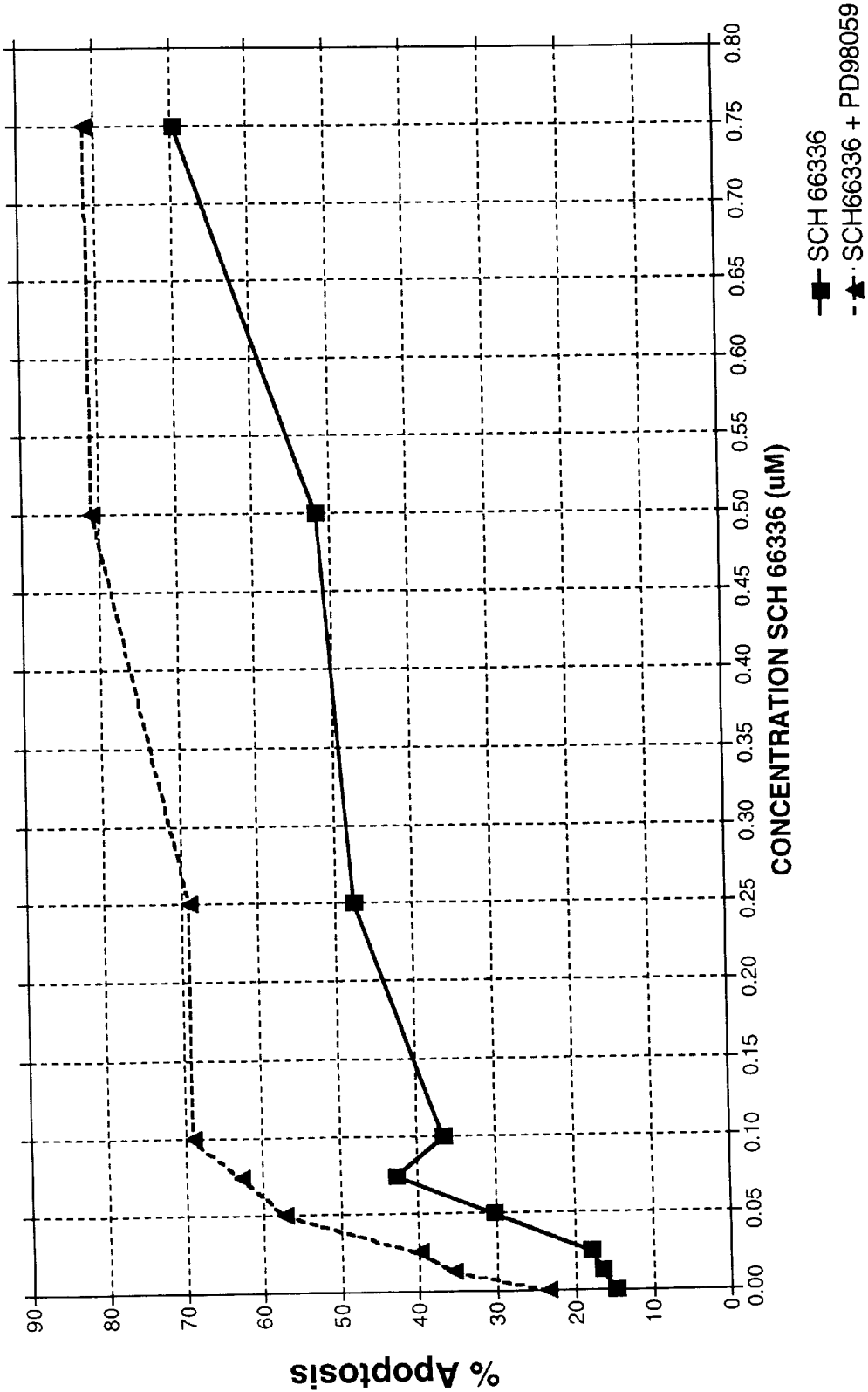

FIG. 3: The dose-dependent apoptotic response to treatment with SCH 66336 is enhanced by addition of PD098059: H-Ras-CVLS-transformed Rat2 cells were treated for 36 hours with the indicated concentrations of SCH 66336, either alone or in a combination with PD098059. Analysis was performed as described in the description for FIG. 2 above. The concentration of SCH 66336 was varied from 0.0125 to 0.75 µM in the presence (▲) or absence (■) of 2.5 µM PD098059.

Figure 4:
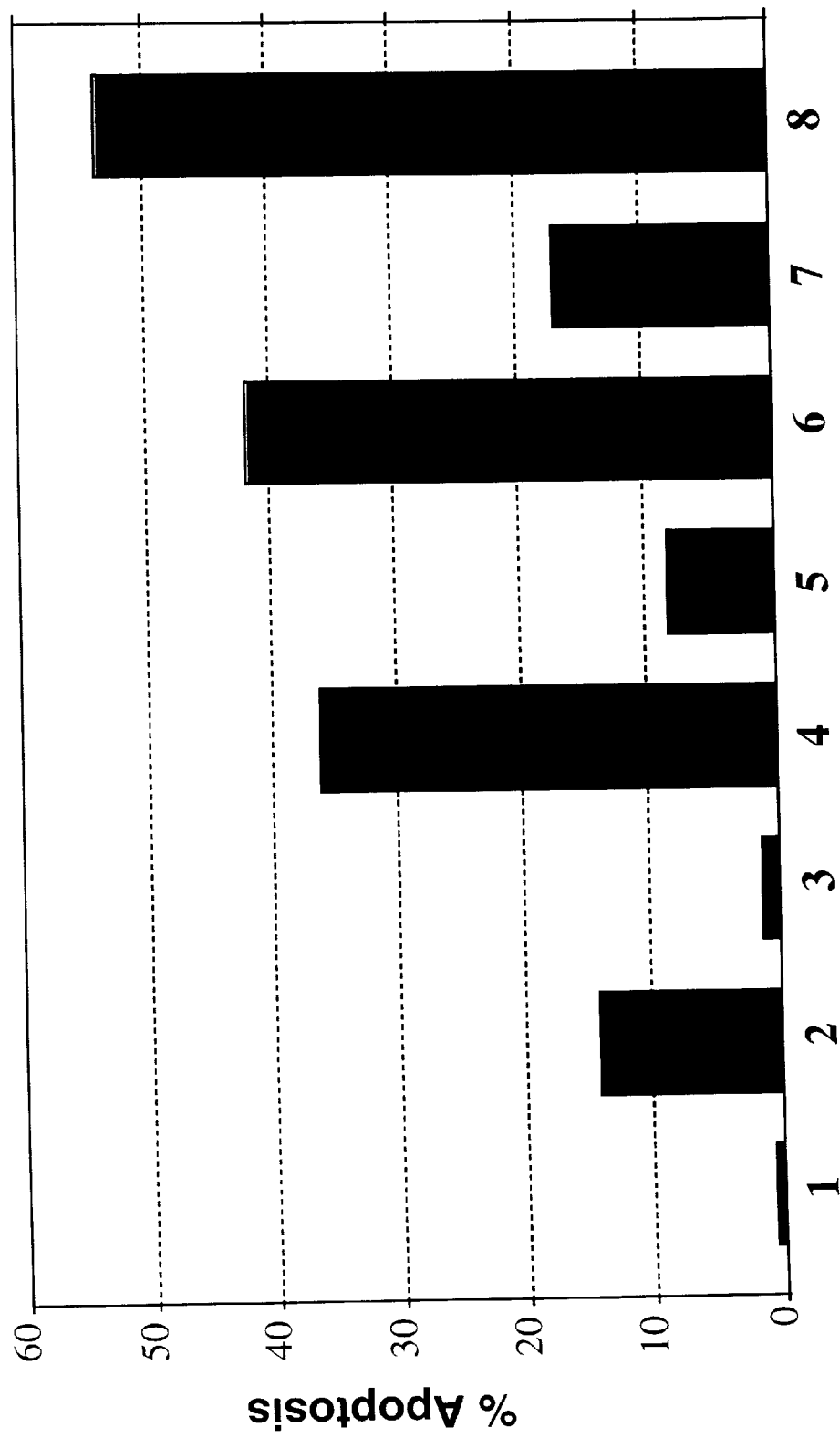

FIG. 4: Effect of SCH 66336 and U0126 on Apoptosis measured by FACS: H-Ras-transformed Rat2 cells were treated for 24 hours with 0 to 10 µM U0126 (#V 1121; Promega Corporation; Madison, Wis.) in the presence or absence of 0.5 µM SCH 66336. Analysis was performed as described in the legend to FIG. 2. 1=Untreated Cells; 2=SCH 66336; 3=1 µM U0126; 4=1 µM U0126+SCH 66336; 5=5 µM U0126; 6=5 µM U0126+SCH 66336; 7=10 µM U0126; 8=10 µM U0126+SCH 66336.

Figure 5:
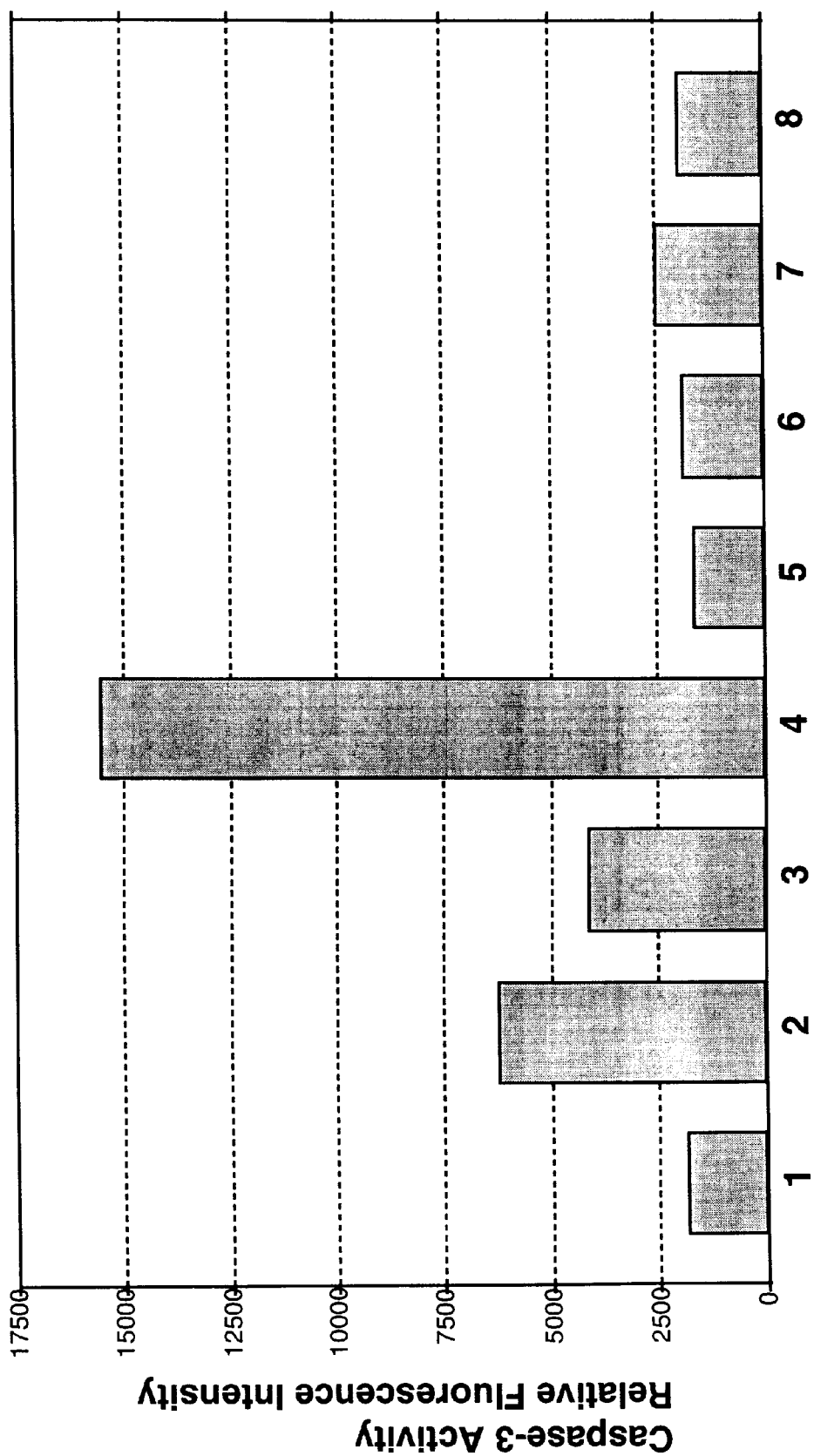

FIG. 5: Effect of SCH 66336 and PD098059 on Apoptosis measured by Caspase Activation: H-Ras-transformed Rat2 and parental Rat2 cells were treated for 24 hours with 20 µM PD098059, 0.5 µM SCH 66336, or a combination of the two drugs. Cells were lysed in a detergent buffer recommended by Clontech (Apo-Alert CPP32/Caspase-3 Assay) and centrifuged at 14,000 rpm for 15 min at 4° C. to pellet the cellular debris. Protein concentration of the resulting supernatant was determined by a BCA protein assay (Pierce; Rockford, Ill.) with 175 µg of each lysate assayed for Caspase-3 activity using a fluorogenic peptide substrate (AC-DEVD-AMC; Clontech; Palo Alto, Calif.) by fluorometry (CytoFluor plate reader; Perseptive Biosystems; Framingham, Mass.). 1=Untreated H-ras Cells; 2=H-ras cells+SCH 66336; 3=H-ras cells+PD09059; 4=H-ras cells+SCH 66336+PD 098959: 5=Untreated Rat2 Cells; 6=Rat2 cells+SCH 66336; 7=Rat2 cells+PD09059; 8=Rat2 cells+SCH 66336+PD 098959.

Figure 6:
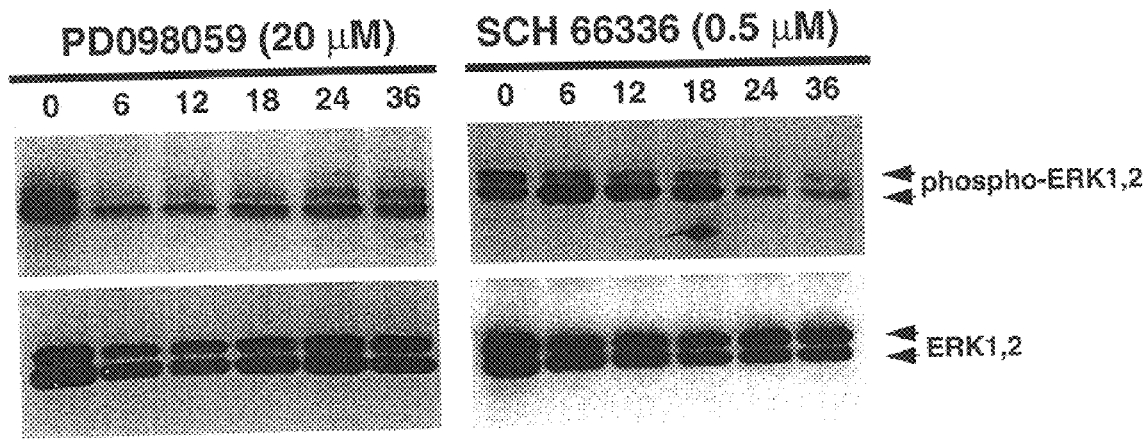

FIG. 6: Effect of SCH 66336 and PD098059 on ERK1 and ERK2 phosphorylation: H-Ras-transformed Rat2 cells were treated with 20 µM PD098059 or 0.5 µM SCH 66336 for 0 to 36 hr. Cells were lysed in a detergent buffer and centrifuged at 14,000 rpm for 15 min at 4° C. to pellet the cellular debris. Protein concentration of the resulting supernatant was determined by a BCA protein assay (Pierce; Rockford, Ill.). Cellular proteins (20 µg) were separated by 8–16% Tris-Glycine polyacrylamide gel electrophoresis (Novex; San Diego, Calif.). Proteins were then transferred to PVDF membranes for Western Blot analysis. Phosphorylated ERK1 and ERK2 were detected using a rabbit polyclonal antibody specific for the phosphorylated p42/44 MAPK proteins (phospho-Thr202/Tyr204 specific; #9101; New England Biolabs, Inc.; Beverly Mass.). Total ERK1 and ERK2 were detected using a rabbit polyclonal antibody specific for the p42/44 MAPK proteins (#9102; New England Biolabs, Inc.; Beverly, Mass.). Both antibodies were recognized with Goat anti-Mouse-HRP antibody (horseradish peroxidase; Chemicon; Temecula, Calif.) and visualized by enhanced chemiluminescence (SuperSignal West Pico Chemiluminescent Substrate; Pierce; Rockford, Ill.).

Figure 7:
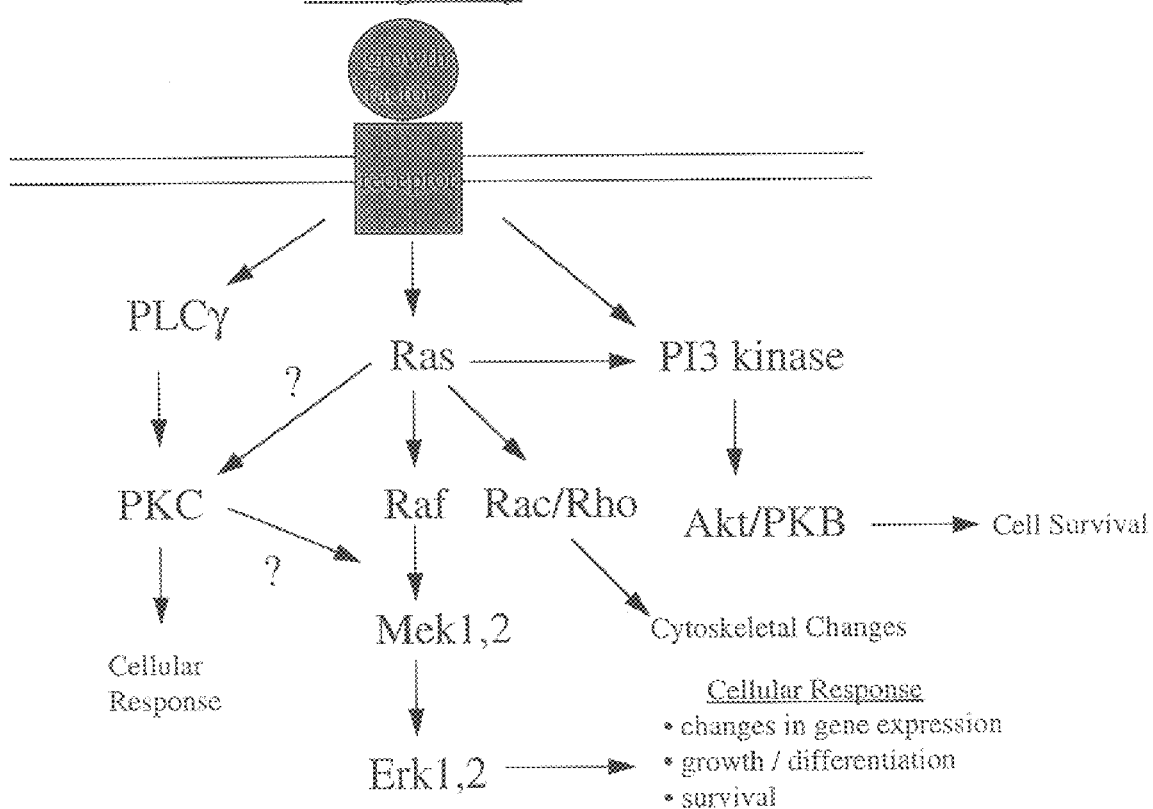

FIG. 7: Intracellular Signal Transduction Pathways: FIG. 1 diagrammed a linear pathway leading from growth factor receptors through Ras to activation of the MAPK cascade. It is clear that signaling pathways are considerably more complex with multiple branches and interconnections. Some of this complexity is illustrated here in FIG. 7.

DETAILED DESCRIPTION OF THE INVENTION

The present invention provides novel methods of treating cancer by combining (1) a farnesyl protein transferase (FPT) inhibitor, and (2) an additional Ras pathway signaling inhibitor.

(1) A "farnesyl protein transferase inhibitor" or "FPT inhibitor" or "FTI" is defined herein as a compound which: (i) potently inhibits FPT (but preferably not geranylgeranyl protein transferase I, in vitro); (ii) blocks the phenotypic change induced by a form of transforming H-ras which is a farnesyl acceptor (but preferably not by a form of transforming H-ras engineered to be a geranylgeranyl acceptor); (iii) blocks intracellular farnesylation of ras; and (iv) blocks abnormal cell growth.

(2) A "Ras signaling pathway inhibitor" is defined herein as an agent that blocks the activity of any protein in the signal transduction pathway shown in FIG. 1. A particularly preferred Ras signaling pathway inhibitor is a "MEK inhibitor", which is defined herein as an agent that blocks the in vitro enzyme activity of a MEK (MAPK/ERK kinase) protein (preferably inhibiting MEK1 and MEK2), and thus blocks the activation of a MAPK protein as evidenced by a block in the phosphorylation of the MAPK protein. This can be detected by western blot analysis for phosphorylated MAPK as described in, e.g., Dudley et al., Proc Natl Acad Sci. 92:7686–7689 (1995), and Favata et al., J Biol Chem. 273:18623–32 (1998).

1. FPT Inhibitors

As single agents, or in combination with chemotherapy (see, e.g., Liu et al., 1998), FPT inhibitors represent a leading approach for blocking the function of Ras oncoproteins. FPT catalyzes the addition of an isoprenyl lipid moiety onto a cysteine residue present near the carboxy-terminus of the Ras protein. This is the first step in a post-translational processing pathway that is essential for both Ras membrane-association and Ras-induced oncogenic transformation. A number of FPT inhibitors have been reported, including a variety of peptidomimetic inhibitors as well as other small molecule inhibitors, most notably the tricyclic FPT inhibitors exemplified by SCH 66336. FPT inhibitors interfere with the post-translational processing of Ras proteins in cells and demonstrate antitumor activity in a wide variety of in vitro and in vivo cancer models (Bishop et al., 1995; Liu et al., 1998). The antitumor activity of SCH 66336 includes inhibition of anchorage-independent growth of a variety of human tumor cell lines in vitro and their growth as xenografts in immuno-compromised mice (Liu et al., 1998). Human tumor cell lines differ significantly in their sensitivity to the growth effects of FPT inhibitors. Sensitivity or resistance does not correlate with Ras mutational status.

In several transgenic mouse tumor models (e.g. MMTV-H-Ras, WAP-H-Ras, TGFα and TGFα/neu) significant tumor regressions are induced by treatment with FPT inhibitors. These regressions are associated with an increase in apoptosis (Liu et al 1998; Barrington et al., 1998; Norgaard et al., 1999). FPT inhibitors can also induce apoptosis of transformed cells in culture. The apoptotic effect in vitro has been reported to require growth in low serum or forced growth in suspension (Hung and Chaung, 1998; Lebowitz et al., 1997; Suzuki et al., 1998).

It has also been shown that FPT inhibitor treatment reduces the activity of the MAPK pathway in Ha-Ras-transformed Rat1 cells (e.g. James et al., 1994). This decrease in MAPK activity correlates with a decrease in cell growth. FPT inhibitors did not reduce MAPK activity in untransformed Rat1cells.

2. Agents Targeting MEK:

The MAPK pathway has also been examined as a target for the development of anti-cancer therapeutics and the effects of specific inhibitors of this pathway on tumor cell lines have been described (Dudley et al., 1995; Favata et al., 1998). The best-characterized MEK inhibitor is PD098059, a small molecule that inhibits the activity of MEK1 and MEK2 via direct binding in a manner that is non-competitive with respect to either substrate (ATP or ERK protein). This results in decreased MEK1 and MEK2 phosphorylation and decreased activation of the MEK substrates, ERK1 and ERK2. PD098059 treatment blocks growth factor-mediated proliferation and anchorage-independent growth of Ras-transformed cells (Alessi et al., 1995).

Recently, a novel MEK inhibitor, U0126, was reported which binds to MEK with a higher affinity than PD098059 (Favata et al., 1998). For more detailed information on MEK inhibitors, and methods of preparing MEK inhibitors, reference can be made, e.g., to international patent publications WO 99/01421 (Jan. 14, 1999) and WO 99/01426 (Jan. 14, 1999).

3. Agents Targeting Growth Factor Receptors:

Two primary approaches have been taken to block growth factor receptor signaling pathways: (i) monoclonal antibodies directed against the receptor; (ii) inhibitors of the receptor tyrosine kinase activity; and (iii) antisense nucleic acids to block protein expression. Anti-receptor monoclonal antibodies include those targeting the erbB2 receptor (e.g. Genentech's Herceptin) and those targeting the EGF receptor. The best characterized anti-EGF receptor antibody is the chimeric antibody C225 (Goldstein et al., 1995). Both Herceptin and C225 have demonstrated efficacy in preclinical tumor models in which their cognate receptors are expressed.

Small molecule inhibitors of tyrosine kinase activity have also been reported with at least two of these compounds already in human clinical trials: Sugen's PDGF receptor inhibitor, SU101, which is in phase III clinical trials for glioma and earlier stage trials for other cancer indications, and Pfizer's EGF receptor inhibitor, CP-358,774, which is in early phase clinical trials (Moyer et al., 1997).

4. Other Signaling Antagonists:

In addition to the approaches described above, other elements of the Ras signaling pathway and other signal transduction pathways have been targeted for cancer drug discovery. The SH2 proteins (SHC and Grb2), which link growth factor receptors to Ras activation, have been targeted by peptidomimetic agents that block the binding of SH2 domains to phosphotyrosine-containing protein sequences.

The protein kinase Raf, which links Ras to MEK1,2 activation, has also been targeted both by small molecule kinase inhibitors and by antisense approaches. The latter approach (ISIS-5132) is in phase II clinical trials (Monia et al., 1996).

Other relevant intracellular signaling targets include the phospho-lipid kinase PI3K (phosphatidylinositol-3 kinase) and protein kinase C.

In preferred embodiments, the methods of the present invention can be used to treat tumorigenic cancer cells by having a significant effect on cell death (e.g. by apoptosis) in the case of the cancerous cells (i.e., having a significant effect on cell death beyond mere arrest of growth) while, at the same time, the active agents can be administered in relatively low doses (and/or less frequently) to minimize potential toxic side effects against normal, untransformed cells. In addition, the present invention provides new methods of treating cancer by providing a longer, more sustained effect on blocking cell signaling, while, at the same time, minimizing the risk of potential toxic side effects against normal cells.

Thus, the present invention also provides methods of inducing a synergistic level of cancer cell death (e.g., apoptosis) in a cancer patient, comprising administering, concurrently or sequentially, effective amounts of (1) a FPT inhibitor and (2) an additional Ras signaling pathway inhibitor (i.e., in amounts sufficient to induce a synergistic level of cancer cell death as measured, e.g., by the propidium iodide fluorescence assay described in Dengler et al., (1995) Anti-cancer Drugs. 6:522–32. Similarly, methods are provided herein for killing cancer cells in a cancer patient (as measured by the assay of Dengler et al 1995) comprising administering effective amounts of (1) a FPT inhibitor and (2) an additional Ras signaling pathway inhibitor.

Furthermore, in preferred embodiments, the methods of the present invention include methods for treating tumors and regressing tumor volume (e.g., as measured by CAT scan) in a patient in need of such treatment (e.g., a mammal such as a human) by administering, concurrently or sequentially, (1) an FPT inhibitor and (2) an additional Ras signaling pathway inhibitor in amounts sufficient to achieve. Examples of tumors which may be treated include, but are not limited to, epithelial cancers, e.g., prostate cancer, lung cancer (e.g., lung adenocarcinoma), pancreatic cancers (e.g., pancreatic carcinoma such as, for example, exocrine pancreatic carcinoma), breast cancers, colon cancers (e.g., colorectal carcinomas, such as, for example, colon adenocarcinoma and colon adenoma), ovarian cancer, bladder carcinoma, and cancers of the liver. Other cancers that can be treated include melanoma, myeloid leukemias (for example, acute myelogenous leukemia), sarcomas, thyroid follicular cancer, and myelodysplastic syndrome.

Pharmaceutical compositions comprising an FPT inhibitor and an additional Ras signaling pathway inhibitor, for the treatment of cancer (including induction of cancer cell death and tumor regression), and preparation of such compositions, are also provided by the present invention.

As used herein the following terms have the following meanings unless indicated otherwise:

"Growth factor receptor inhibitor": an agent that blocks the signal transduction properties of a growth factor receptor. These may act as direct inhibitors of the receptor's tyrosine kinase activity or by inhibiting ligand-stimulated activation of the receptor kinase activity as described in Levitzki and Gazit, 1995.

"Trosine kinase inhibitor": an agent that blocks the tyrosine phosphorylation activity by either being competitive with ATP or via an allosteric interaction with the enzyme as described in Levitzki and Gazit, 1995.

"Protein kinase inhibitor": an agent that blocks protein phosphorylation activity on serine, threonine, or tyrosine residues as described in Levitzki and Gazit, 1995.

"p185 erbB2/HER2/neu receptor inhibitor" or "erbB2 receptor inhibitor": an agent that blocks the signal transduction properties of the erbB2 receptor by either inhibiting the receptor's tyrosine kinase activity or blocking ligand-stimulation of the receptor's kinase activity as described in Levitzki and Gazit, 1995.

"PDGF receptor tyrosine kinase inhibitor": an agent that blocks the signal transduction properties of the platelet-derived growth factor (PDGF) receptor by either inhibiting the receptor's tyrosine kinase activity or blocking PDGF-stimulation of the receptor's kinase activity as described in Kovalenko et al., 1994.

"EGF receptor tyrosine kinase inhibitor": an agent that blocks the signal transduction properties of the epidermal growth factor (EGF) receptor by either inhibiting the receptor's tyrosine kinase activity or blocking EGF-stimulation of the receptor's kinase activity as described in Fry et al., 1994.

"An antibody directed against the extracellular domain of a growth factor receptor": such antibody blocks the biological activity of the growth factor receptor by inhibiting the binding of ligand and/or preventing ligand-stimulated activation of the receptor tyrosine kinase as described in Mendelson, 1992.

"A monoclonal antibody which targets the p185 erbB2/HER2/neu receptor" or "A monoclonal antibody which targets the erbB2 receptor": such antibody blocks the biological activity of the HER2 receptor as shown by inhibiting the binding of ligand and/or preventing ligand-stimulated activation of the growth factor receptor kinase as described in Pegram et al., 1998.

"A monoclonal antibody which targets the EGF receptor": shown by a monoclonal antibody which inhibits EGF binding and/or EGF-stimulated kinase activity as described in Mendelson, 1992.

"An antisense molecule directed against a growth factor receptor or other component in the Ras signal pathway": a modified oligonucleotide which interferes with messenger RNA translation (and hence protein expression) of any protein component in the pathway as described in Wang et al., 1998 or Resnicoff, 1998. For a general discussion of antisense technology, see, e.g., Antisense DNA and RNA, (Cold Spring Harbor Laboratory, D. Melton, ed., 1988).

"Concurrently": (1) simultaneously in time, or (2) at different times during the course of a common treatment schedule; and "Sequentially": (1) administration of one component of the method ((a) FPT inhibitor, or (b) an additional Ras pathway inhibitor) followed by administration of the other component; after administration of one component, the second component can be administered substantially immediately after the first component, or the second component can be administered after an effective time period after the first component; the effective time period is the amount of time given for realization of maximum benefit from the administration of the first component.

"Downstream" is defined herein as a protein activity (within the Ras signaling pathway) which is regulated by Ras either directly via protein:protein binding or indirectly by a Ras-regulated effector protein. Thus, with reference to FIG. 1, an "element downstream from Ras" can be, e.g., Mek1,2 or Erk1,2.

"Upstream" is defined herein as a protein activity (within the Ras signaling pathay) which would regulate the activity of Ras either directly via protein:protein binding or indirectly by regulating another protein which directly binds to and regulates Ras activity. Thus, an "element upstream of Ras" can be, e.g., erbB2 , PDGF receptor, IGF receptor, or EGF receptor.

"Cell death" as described herein is the death of a cell induced either under physiological conditions or by acute injury resulting in the disassembly of the cell organelles and proteins and the abolition of metabolic processes as reviewed in Raff, M. (1998). Nature. 396:119–122. Cell death can be measured, e.g., by the propidium iodide flow cytometry assay described in Dengler et al., (1995) Anticancer Drugs. 6:522–32.

"Apoptosis" as described herein as a form of cell death (programmed cell death) that exhibits stereotypic morphological changes as reviewed in Raff, M. (1998). Nature. 396:119–122. Apoptosis can be measured, e.g., by the propidium iodide flow cytometry assay described in Dengler et al., (1995) Anticancer Drugs. 6:522–32, or by the in situ terminal deoxynucleotidyl transferase and nick translation assay (TUNEL analysis) described in Gorczyca, (1993) Cancer Res 53:1945–51.

"Synergistic" or "synergistic level" is defined herein as an effect achieved by the combination of two components that is greater than the sum of the effects of either of the two components alone (keeping the amount of the component constant). Thus, for example, the phrase "amounts effective to induce a synergistic level of cancer cell death" refers to amounts of two components that achieve a level of cancer cell death (e.g., cell death by apoptosis as measured by the propidium iodide flow cytometry assay described in Dengler et al., (1995) Anticancer Drugs. 6:522–32, or by the in situ terminal deoxynucleotidyl transferase and nick translation assay (TUNEL analysis) described in Gorczyca, (1993) Cancer Res 53:1945–51.), which is greater than the sum of the effects of either of the two components alone.

"Sustained effect" is defined herein as a prolonged/enhanced apoptotic response to combination treatment with a FPT I and a MEK1,2 inhibitor in comparison to single treatment alone. The consequences of a "sustained effect" can be monitored either by measurement of MAPK activity or cell death or apoptosis, as described in previously. The effective time course for inhibition of MAPK pathway by the individual drugs is dose dependent. However, the experiments herein show that the MEK1,2 inhibitors optimally inhibit the MAPK pathway at or prior to 6 hr of treatment, while SCH 66336 demonstrates optimal MAPK pathway inhibition 12–18 hr after treatment. The MAPK inhibitory effect of SCH 66336 has been shown to last as long as 72 hr after treatment. Thus, combination of the two drugs can result in a "sustained" inhibition of the MAPK pathway for a long period of time, preferably for a period starting at or just prior to 6 hours after treatment, and preferably continuing through to 36 hours, more preferably 72 hours, post treatment. (See, e.g., FIG. 6).

The phrase "killing cancer cells" means induction of cancer cell death of transformed, tumorigenic cancer cells.

MORE DETAILED ILLUSTRATIONS OF FPT INHIBITORS

Classes of compounds that can be used as the FPT inhibitor include: fused-ringed tricyclic benzocycloheptapyridines, oligopeptides, peptido-mimetic compounds, farnesylated peptido-mimetic compounds, carbonyl piperazinyl compounds, carbonyl piperidinyl compounds, farnesyl derivatives, and natural products and derivatives.

Examples of compounds that are FPT inhibitors and the documents directed to those compounds are given below.

Fused-ring tricyclic benzocycloheptapyridines: WO 95/10514; WO 95/10515; WO 95/10516; WO 96/30363; WO 96/30018; WO 96/30017; WO 96/30362; WO 96/31111; WO 96/31478; WO 96/31477; WO 96/31505; WO 97/23478; International Patent Application No. PCT/US97/17314 (WO 98/15556); International Patent Application No. PCT/US97/15899 (WO 98/11092); International Patent Application No. PCT/US97/15900 (WO 98/11096); International Patent Application No. PCT/US97/15801 (WO 98/11106); International Patent Application No. PCT/US97/15902 (WO 98/11097); International Patent Application No. PCT/US97/15903 (WO 98/11098); International Patent Application No. PCT/US97/15904; International Patent Application No. PCT/US97/15905 (WO 98/11099); International Patent Application No. PCT/US97/15906 (WO 98/11100); International Patent Application No. PCT/US97/15907 (WO 98/11093); International Patent Application No. PCT/US97/19976 (WO 98/11091); U.S. application Ser. No. 08/877049: U.S. application Ser. No. 08/877366; U.S. application Ser. No. 08/877399; U.S. application Ser. No. 08/877336; U.S application Ser. No. 08/877269; U.S. application Ser. No. 08/877050; U.S application Ser. No. 08/877052; U.S application Ser. No. 08/877051; U.S. application Ser. No. 08/877498; U.S application Ser. No. 08/877057; U.S application Ser. No. 08/877739; U.S. application Ser. No. 08/877677; U.S application Ser. No. 08/877741; U.S application Ser. No. 08/877743; U.S. application Ser. No. 08/877457; U.S application Ser. No. 08/877673; U.S application Ser. No. 08/876507; and U.S. application Ser. No. 09/216,398.

Some FPT inhibitors are oligopeptides, especially tetrapeptides, or derivatives thereof, based on the formula Cys-Xaa$_1$-Xaa$_2$-Xaa$_3$, where Xaa$_3$ represents a serine, methionine or glutamine residue, and Xaa$_1$ and Xaa$_2$ can represent a wide variety of amino acid residues, but especially those with an aliphatic side-chain. Their derivatives may or may not have three peptide bonds; thus it has been found that reduction of a peptide bond —CO—NH— to a secondary amine grouping, or even replacement of the nitrogen atoms in the peptide chain with carbon atoms (provided that certain factors such as general shape of the molecule and separation of the ends are largely conserved) affords compounds that are frequently more stable than the oligopeptides and, if active, have longer activity. Such compounds are referred to herein as peptido-mimetic compounds.

Oligopeptides (mostly tetrapeptides but also pentapeptides) including the formula Cys-Xaa$_1$-Xaa$_2$-Xaa$_3$: EPA 461,489; EPA 520,823; EPA 528,486; and WO 95/11917.

Peptido-mimetic compounds—especially Cys-Xaa-Xaa-Xaa-mimetics: EPA 535,730; EPA 535,731; EPA 618,221; WO 94/09766; WO 94/10138; WO 94/07966; U.S. Pat. No. 5,326,773; U.S. Pat. No. 5,340,828; U.S. Pat. No. 5,420,245; WO 95/20396; U.S. Pat. No. 5,439,918; and WO 95/20396.

Farnesylated peptido-mimetic compounds—specifically farnesylated Cys-Xaa-Xaa-Xaa-mimetic: GB-A 2,276,618.

Other peptido-mimetic compounds: U.S. Pat. No. 5,352,705; WO 94/00419; WO 95/00497; WO 95/09000; WO 95/09001; WO 95/12612; WO 95/25086; EPA 675,112; and FR-A 2,718,149.

Farnesyl derivatives: EPA 534,546; WO 94/19357; WO 95/08546; EPA 537,007; and WO 95/13059.

Natural products and derivatives: WO 94/18157; U.S. Pat. No. 5,430,055; GB-A 2,261,373; GB-A 2,261,374; GB-A 2,261,375; U.S. Pat. No. 5,420,334; U.S. Pat. No. 5,436,263.

Other compounds: WO 94/26723; WO 95/08542; U.S. Pat. No. 5,420,157; WO 95/21815; WO 96/31501; WO 97/16443; WO 97/21701; U.S. Pat. No. 5,578,629; U.S. Pat. No. 5,627,202; WO 96/39137; WO 97/18813; WO 97/27752WO 97/27852; WO 97/27853; WO 97/27854; WO 97/36587; WO 97/36901; WO 97/36900; WO 97/36898; WO 97/36897; WO 97/36896; WO 97/36892; WO 97/36891; WO 97/36890; WO 97/36889; WO 97/36888; WO 97/36886; WO 97/36881; WO 97/36879; WO 97/36877; WO 97/36876; WO 97/36875; WO 97/36605; WO 97/36593; WO 97/36592; WO 97/36591; WO 97/36585; WO 97/36584; and WO 97/36583.

A plasmid encoding an α- and a β-unit of an FPT, and describing an assay therefor: WO 94/10184.

Reference is also made to U.S application Ser. No. 09/217,335 and International Patent Application No. PCT/US98/26224, which disclose a variety of methods for combining FPT inhibitors with chemotherapeutic agents and/or radiation therapy in the treatment of proliferative disease such as cancer.

All of the foregoing documents directed to compounds that are FPT inhibitors are incorporated herein by reference thereto.

A review of many such compounds is given by Graham in *Exp. Opin. Ther. Patents* (1995) 5(12): 1269–1285.

It will be understood that the breadth of a chemical formula in a patent specification may not enable one to classify all compounds therein under one of the headings above. For example, the monoterpenyl chain in the farnesyl derivatives may be extended, e.g. by a number of methylene groups or even another isoprene residue.

The tetrapeptides of the formula Cys-Xaa$_1$-Xaa$_2$-Xaa$_3$ have an amino-terminal cysteine residue. A tetrapeptide of that type forms the carboxyl-terminal of ras. Such tetrapeptides are capable of binding with FPT and competing with ras. Compounds of similar structure but having at least one of the carbonyl groups of the tetrapeptide replaced by a hydrocarbyl group such as a methylene group and classified above as peptido-mimetic compounds are also capable of binding with FPT and competing with ras, but are generally more resistant to enzymatic degradation in vivo.

FPT INHIBITORS—EXEMPLIFIED COMPOUNDS

The following documents disclose preferred FPT inhibitors for use in the present invention. The documents also disclose methods of inhibiting abnormal cell growth (e.g., tumors) using the compounds disclosed in the document. The radicals and formulae designations defined herein for a particular document apply only to the compounds described in that document.

WO 95/10516 published Apr. 20, 1995 and WO 96/30363 published Oct. 3, 1996 disclose compounds of formula 1.0:

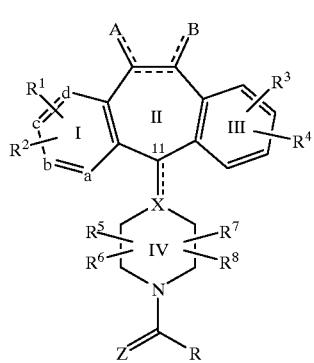

(1.0)

or a pharmaceutically acceptable salt or solvate thereof, wherein:

one of a, b, c and d represents N or $NR^9$ wherein $R^9$ is O—, —$CH_3$ or —$(CH_2)_nCO_2H$ wherein n is 1 to 3, and the remaining a, b, c and d groups represent $CR^1$ or $CR^2$; or each of a, b, c, and d is independently selected from $CR^1$ and $CR^2$;

each $R^1$ and each $R^2$ is independently selected from H, halo, —$CF_3$, —$OR^{10}$, —$COR^{10}$, —$SR^{10}$, —$S(O)_tR^{11}$ (wherein t is 0, 1 or 2), —SCN, —$N(R^{10})_2$, —$NO_2$, —$OC(O)R^{10}$, —$CO_2R^{10}$, —$OCO_2R^{11}$, —CN, —NHC(O)$R^{10}$, —$NHSO_2R^{10}$, —$CONHR^{10}$, —$CONHCH_2CH_2OH$, —$NR^{10}COOR^{11}$, —$SR^{11}C(O)OR^{11}$,

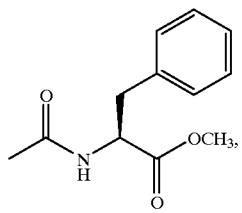

—$SR^{11}N(R^{75})_2$ (wherein each $R^{75}$ is independently selected from H and —$C(O)OR^{11}$), benzotriazol-1-yloxy, tetrazol-5-ylthio, substituted tetrazol-5-ylthio, alkynyl, alkenyl and alkyl, said alkyl or alkenyl group optionally being substituted with halo, —$OR^{10}$ or —$CO_2R^{10}$;

$R^3$ and $R^4$ are the same or different and each independently represents H or any of the substituents of $R^1$ and $R^2$, or $R^3$ and $R^4$ taken together represent a saturated or unsaturated $C_5$–$C_7$ ring fused to the benzene ring;

each of $R^5$, $R^6$, $R^7$ and $R^8$ independently represents H, —$CF_3$, —$COR^{10}$, alkyl or aryl, said alkyl or aryl optionally being substituted with —$OR^{10}$, —$SR^{10}$, —$S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$, or $OPO_3R^{10}$, or one of $R^5$, $R^6$, $R^7$ and $R^8$ can be taken in combination with $R^{40}$ as defined below to represent —$(CH_2)_r$— wherein r is 1 to 4 which can be substituted with lower alkyl, lower alkoxy, —$CF_3$ or aryl, or $R^5$ is combined with $R^6$ to represent =O or =S and/or $R^7$ is combined with $R^8$ to represent =O or =S;

$R^{10}$ represents H, alkyl, aryl, or aralkyl;

$R^{11}$ represents alkyl or aryl;

X represents N, CH or C, which C may contain an optional double bond, represented by the dotted line, to carbon atom 11;

the dotted line between carbon atoms 5 and 6 represents an optional double bond, such that when a double bond is present, A and B independently represent —$R^{10}$, halo, —$OR^{11}$, —$OCO_2R^{11}$ or —$OC(O)R^{10}$, and when no double bond is present between carbon atoms 5 and 6, each of A and B independently represents $H_2$, —$(OR^{11})_2$, (H and halo), dihalo, (alkyl and H), (alkyl)$_2$, (H and —$OC(O)R^{10}$), (H and —$OR^{10}$), =O, (aryl and H), =$NOR^{10}$, or —O—$(CH_2)_p$—O— wherein p is 2, 3 or 4;

R represents $R^{40}$, $R^{42}$, $R^{44}$, or $R^{54}$, as defined below:

$R^{40}$ represents H, aryl, alkyl, cycloalkyl, alkenyl, alkynyl or —D wherein —D represents

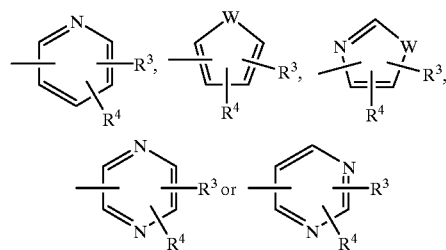

wherein $R^3$ and $R^4$ are as previously defined and W is O, S or $NR^{10}$ wherein $R^{10}$ is as defined above; said $R^{40}$ cycloalkyl, alkenyl and alkynyl groups being optionally substituted with from 1–3 groups selected from halo, —$CON(R^{10})_2$, aryl, —$CO_2R^{10}$, —$OR^{12}$, —$SR^{12}$, —$N(R^{10})_2$, —$N(R^{10})CO_2R^{11}$, —$COR^{12}$, —$NO_2$ or D, wherein —D, $R^{10}$ and $R^{11}$ are as defined above and $R^{12}$ represents $R^{10}$, —$(CH_2)_mOR^{10}$ or —$(CH_2)_qCO_2R^{10}$ wherein $R^{10}$ is as previously defined, m is 1 to 4 and q is 0 to 4; said alkenyl and alkynyl $R^{40}$ groups not containing —OH, —SH or —$N(R^{10})_2$ on a carbon containing a double or triple bond respectively; or $R^{40}$ represents phenyl substituted with a group selected from —$SO_2NH_2$, —$NHSO_2CH_3$, —$SO_2NHCH_3$, —$SO_2CH_3$, —$SOCH_3$, —$SCH_3$, and —$NHSO_2CF_3$, which group is preferably located in the para position of the phenyl ring; or $R^{40}$ represents a group selected from

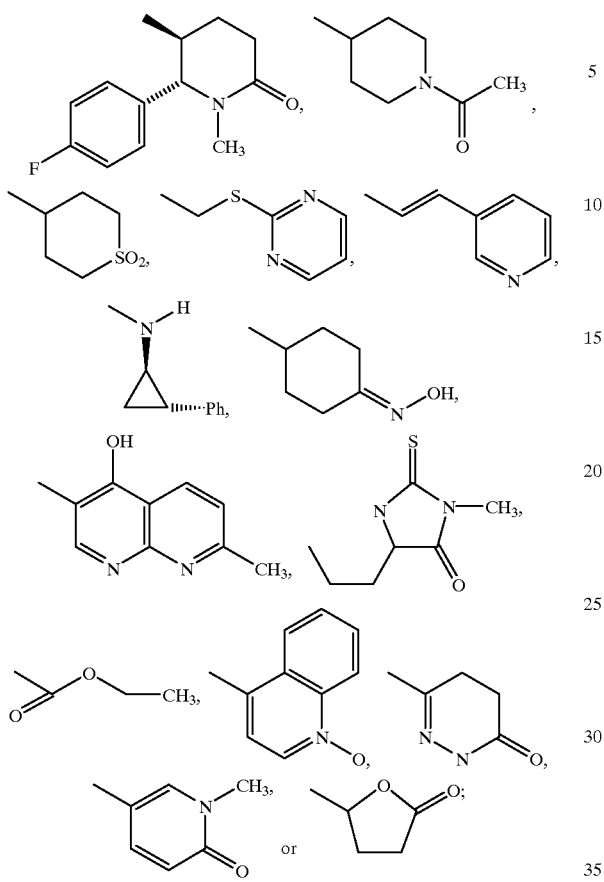

or $R^{42}$ represents

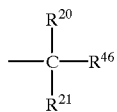

Wherein $R^{20}$, $R^{21}$ and $R^{46}$ are each independently selected from the group consisting of:
(1) H;
(2) —$(CH_2)_q SC(O)CH_3$ wherein q is 1 to 3;
(3) —$(CH_2)_q OSO_2CH_3$ wherein q is 1 to 3;
(4) —OH;
(5) —CS—$(CH_2)_w$-(substituted phenyl) wherein w is 1 to 3 and the substitutents on said substituted phenyl group are the same substituents as described under (12) below for substituted phenyl;
(6) —$NH_2$;
(7) —NHCBZ;
(8) —$NHC(O)OR^{22}$ wherein $R^{22}$ is an alkyl group having from 1 to 5 carbon atoms, or $R^{22}$ represents phenyl substituted with 1 to 3 alkyl groups;
(9) alkyl;
(10) —$(CH_2)_k$-phenyl wherein k is 1 to 6;
(11) phenyl;
(12) substituted phenyl wherein the substituents are selected from the group consisting of: halo, $NO_2$, —OH, —$OCH_3$, —$NH_2$, —$NHR^{22}$, —$N(R^{22})_2$, alkyl, —$O(CH_2)_t$-phenyl (wherein t is from 1 to 3), and —$O(CH_2)_t$-substituted phenyl (wherein t is from 1 to 3);

(13) naphthyl;
(14) substituted naphthyl, wherein the substituents are as defined for substituted phenyl under (12) above;
(15) bridged polycyclic hydrocarbons having from 5 to 10 carbon atoms;
(16) cycloalkyl having from 5 to 7 carbon atoms;
(17) heteroaryl;
(18) hydroxyalkyl;
(19) substituted pyridyl or substituted pyridyl N-oxide wherein the substituents are selected from methylpyridyl, morpholinyl, imidazolyl, 1-piperidinyl, 1-(4-methylpiperazinyl), —$S(O)_tR^{11}$, and any of the substituents given under (12) above for substituted phenyl, and said substitutents are bound to a ring carbon by replacement of the hydrogen bound to said carbon;

(20)

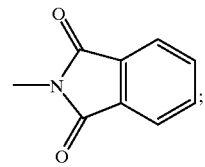

(21)

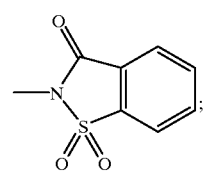

(22)

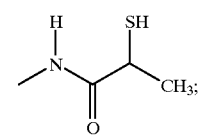

(23) —NHC(O)—$(CH_2)_k$-phenyl or —NH(O)—$(CH_2)_k$-(substituted phenyl), wherein said k is as defined under (10) above;
(24) piperidine Ring V:

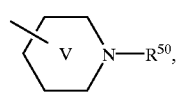

wherein $R^{50}$ represents H, alkyl, alkylcarbonyl, alkoxycarbonyl, haloalkyl, or —$C(O)NH(R^{10})$ wherein $R^{10}$ is H or alkyl;
(25) —$NHC(O)CH_2C_6H_5$ or —$NHC(O)CH_2$-(substituted $C_6H_5$);
(26) —$NHC(O)OC_6H_5$;

(27)

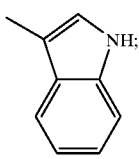

-continued

(28)
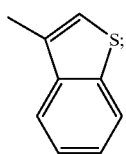

(29)
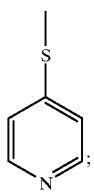

(30) —OC(O)-heteroaryl (for example pyridine-4-carbonyloxy);
(31) —O—alkyl (e.g., —OCH$_3$);
(32) —CF$_3$;
(33) —CN;
(34) a heterocycloalkyl group of the formula

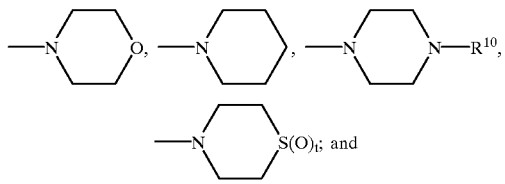

(35) a piperidinyl group of the formula

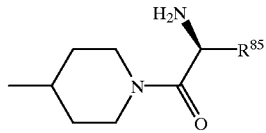

Wherein R$^{85}$ is H, alkyl, or alkyl substituted by —OH or —SCH$_3$; or

R$^{20}$ and R$^{21}$ taken together form an =O group and the remaining R$^{46}$ is as defined above; or two of R$^{20}$, R$^{21}$ and R$^{46}$ taken together form piperidine Ring V

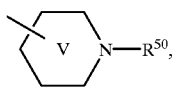

wherein R$^{50}$ is as defined under (24) above;
with the proviso that R$^{46}$, R$^{20}$ and R$^{21}$ are selected such that the carbon atom to which they are bound is not bonded to more than one heteroatom;

R$^{44}$ represents —NR$^{25}$R$^{48}$ wherein R$^{25}$ represents heteroaryl, N-methylpiperidinyl or aryl, and R$^{48}$ represents H or alkyl;

R$^{54}$ represents an N-oxide heterocyclic group of the formula (i), (ii), (iii) or (iv):

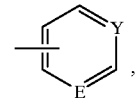
(i)

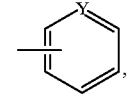
(ii)

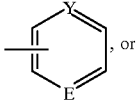
(iii)

or

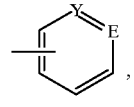
(iv)

wherein R$^{56}$, R$^{58}$, and R$^{60}$ are the same or different and each is independently selected from H, halo, —CF$_3$, —OR$^{10}$, —C(O)R$^{10}$, —SR$^{10}$, —S(O)$_e$R$^{11}$ (wherein e is 1 or 2), —N(R$^{10}$)$_2$, —NO$_2$, —CO$_2$R$^{10}$, —OCO$_2$R$^{11}$, —OCOR$^{10}$, alkyl, aryl, alkenyl and alkynyl, which alkyl may be substituted with —OR$^{10}$, —SR$^{10}$ or —N(R$^{10}$)$_2$ and which alkenyl may be substituted with OR$^{11}$ or SR$^{11}$; or R$^{54}$ represents an N-oxide heterocyclic group of the formula (ia), (iia), (iiia) or (iva):

(ia)

(iia)

(iiia)
or (iva)

wherein Y represents N$^+$—O$^-$ and E represents N; or
R$^{54}$ represents an alkyl group substituted with one of said N-oxide heterocyclic groups (i), (ii), (iii), (iv), (ia), (iia), (iiia) or (iva); and
Z represents O or S such that R can be taken in combination with R$^5$, R$^6$, R$^7$ or R$^8$ as defined above, or R represents R$^{40}$, R$^{42}$, R$^{44}$ or R$^{54}$.

WO 97/23478 published Jul. 3, 1997, and expressly incorporated herein by reference, discloses the compounds:
(1.0)
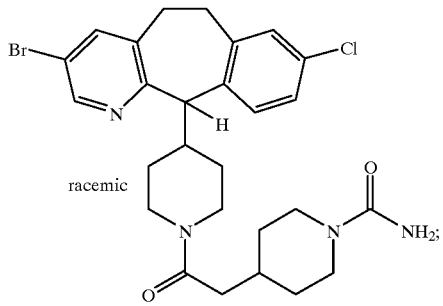
(2.0)
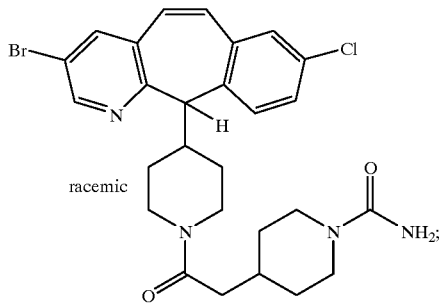
(3.0)
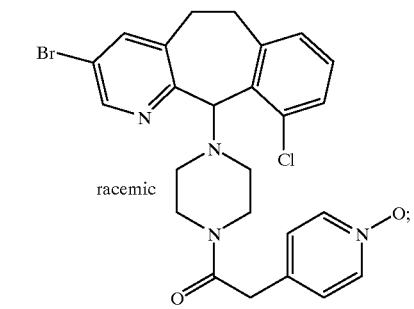
(5.0)
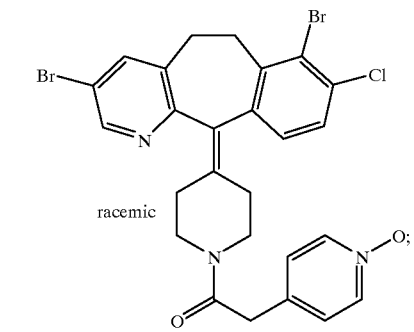
(6.0)
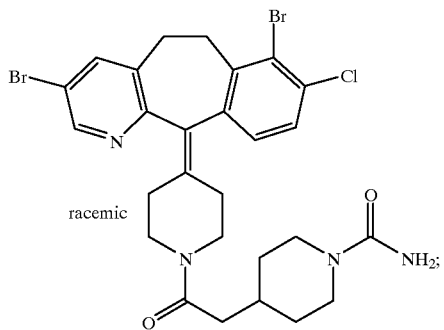
(7.0)
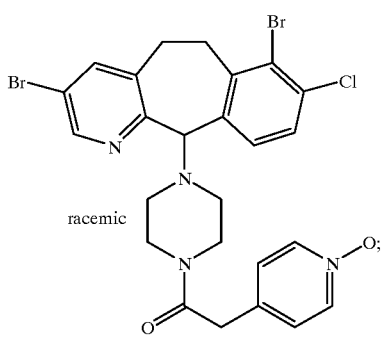
(7.0A)
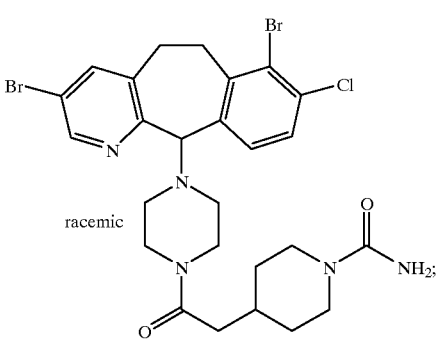
(8.0)
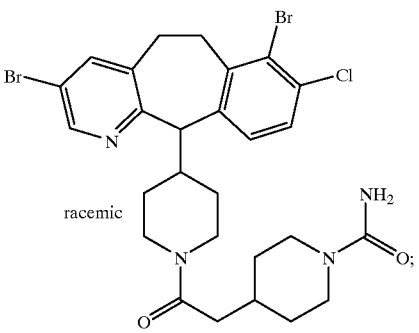

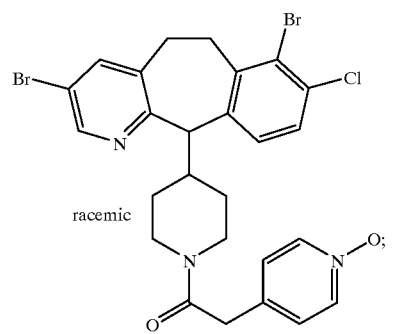
(8.0A)
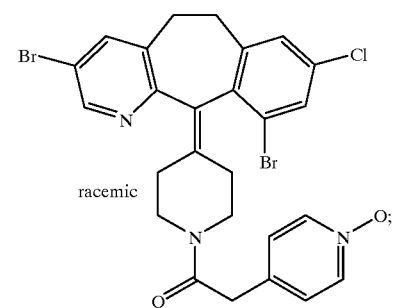
(9.0)
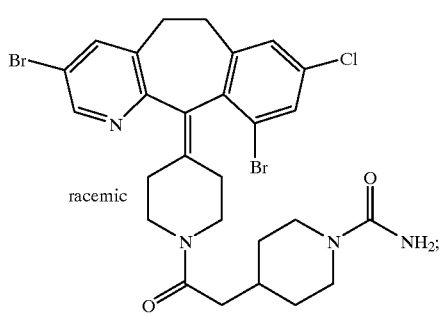
(10.0)
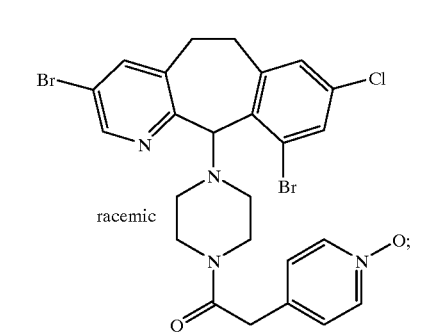
(11.0)
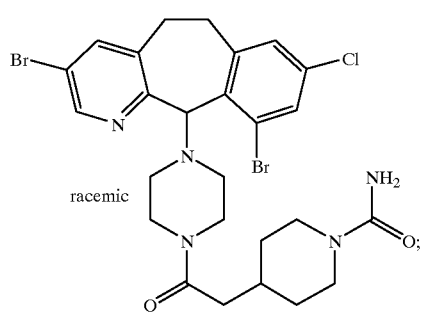
(12.0)
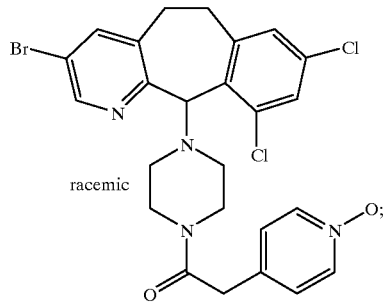
(13.0)
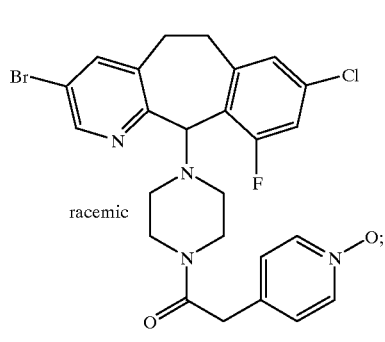
(14.0)
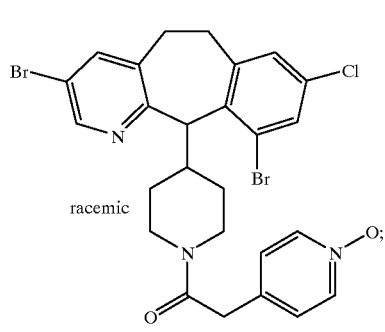
(15.0)
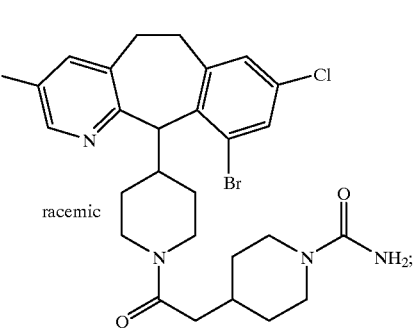
(16.0)
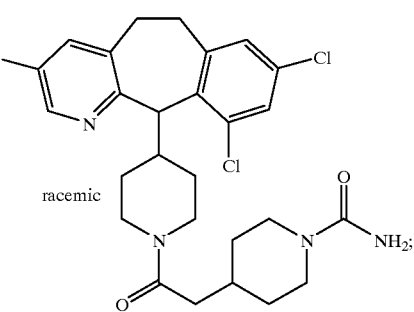
(17.0)

-continued
(18.0)
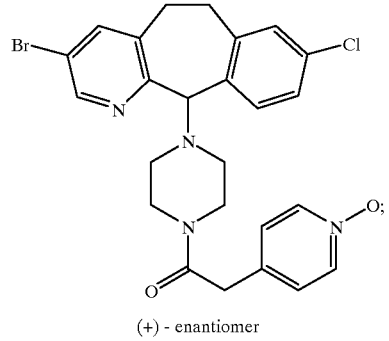
(+) - enantiomer
(19.0)
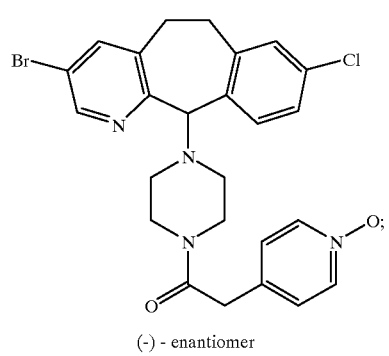
(-) - enantiomer
(20.0)
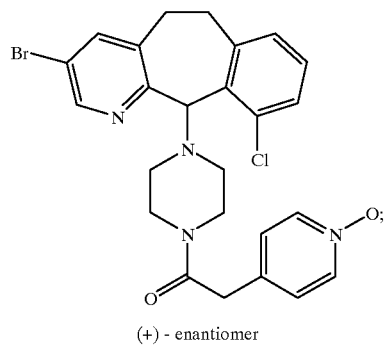
(+) - enantiomer
(21.0)
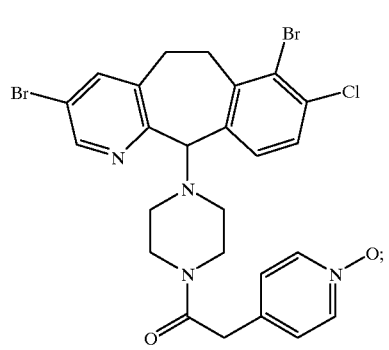
(+) - enantiomer
-continued
(22.0)
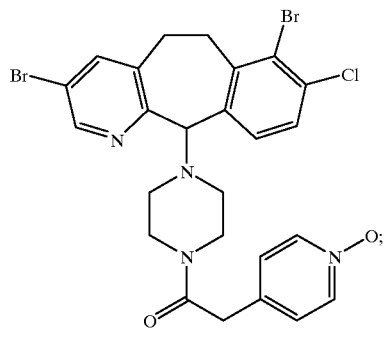
(-) - enantiomer
(23.0)
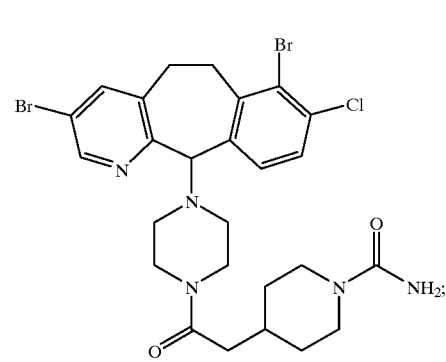
(-) - enantiomer
(24.0)
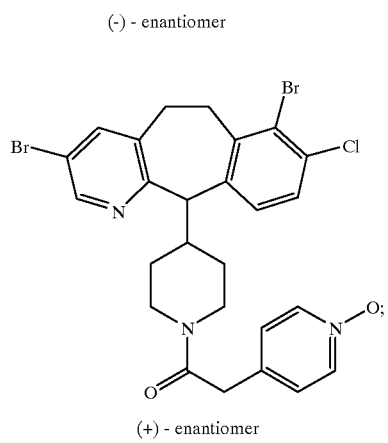
(+) - enantiomer
(25.0)
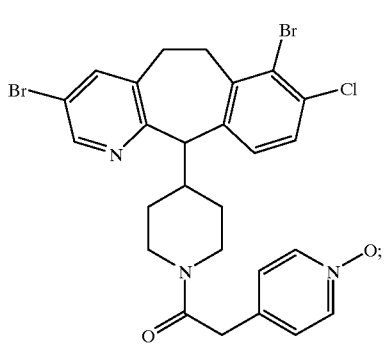
(-) - enantiomer (26.0) (+)-enantiomer (27.0) (−)-enantiomer (28.0) (−)-enantiomer (29.0) (+)-enantiomer (30.0) (−)-enantiomer (31.0) (+)-enantiomer (32.0) (+)-enantiomer (33.0) (−)-enantiomer

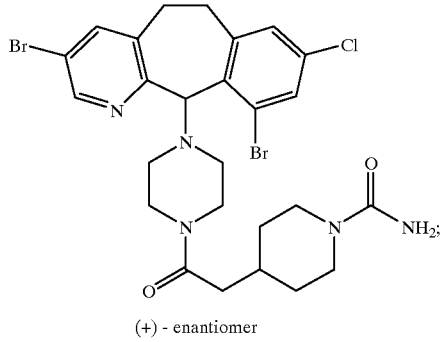
(34.0)
(+) - enantiomer
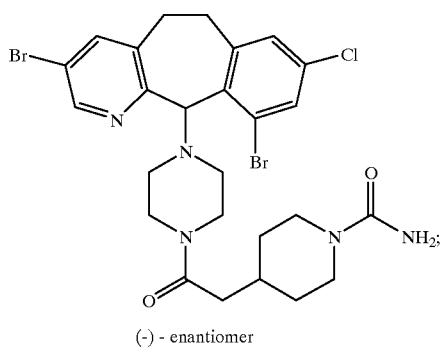
(35.0)
(-) - enantiomer
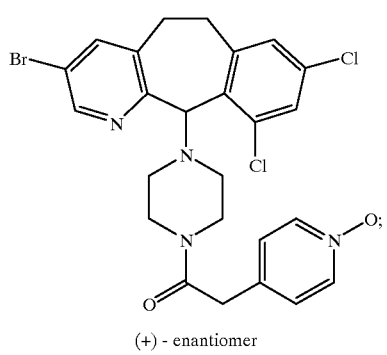
(36.0)
(+) - enantiomer
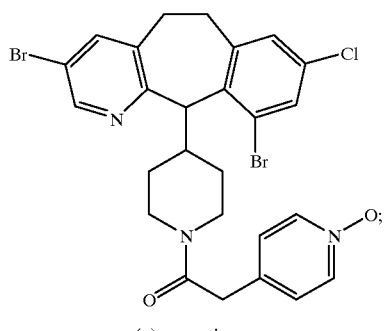
(37.0)
(+) - enantiomer
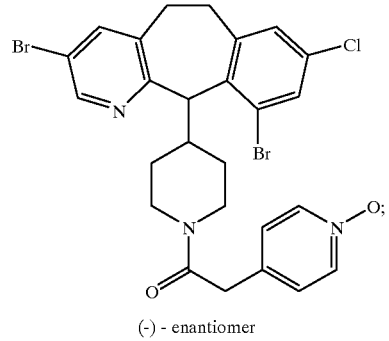
(38.0)
(-) - enantiomer
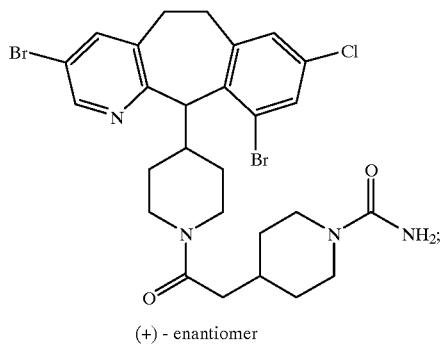
(39.0)
(+) - enantiomer
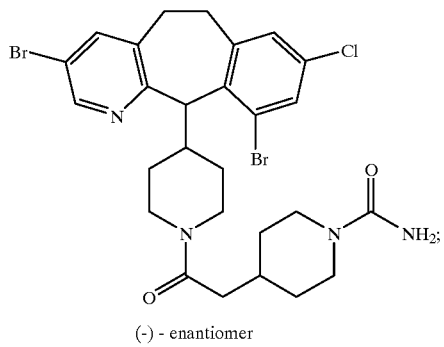
(40.0)
(-) - enantiomer
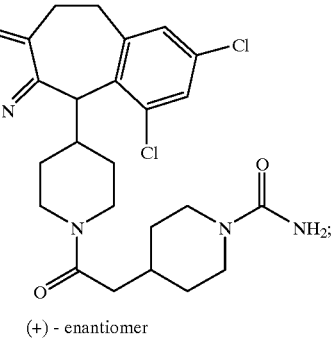
(41.0)
(+) - enantiomer -continued
(42.0)
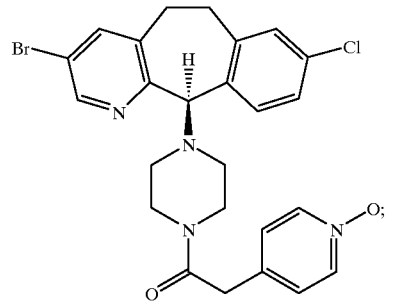
(43.0)
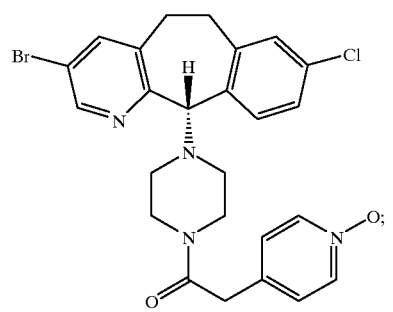
(44.0)
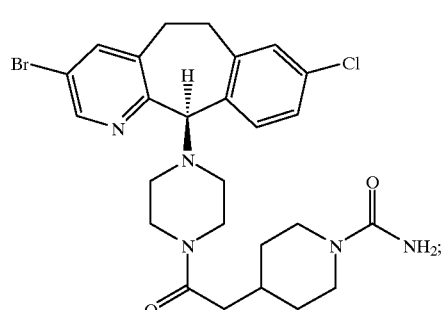
(45.0)
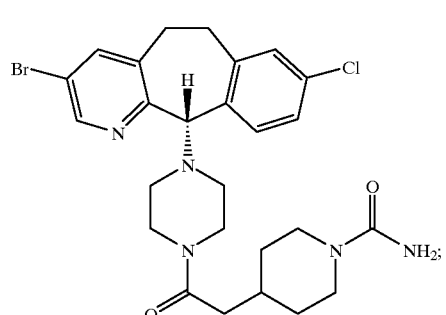
(46.0)
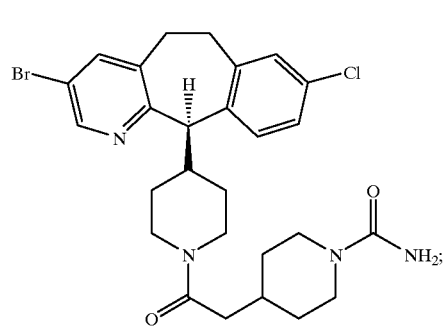
(47.0)
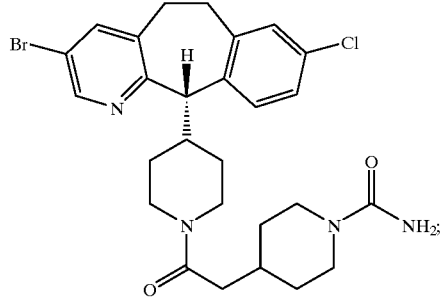
(48.0)
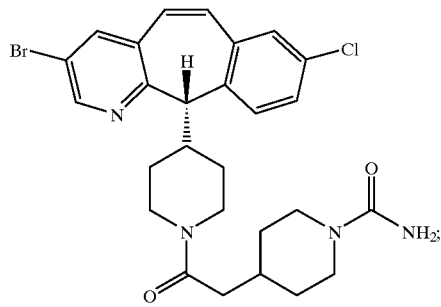
(49.0)
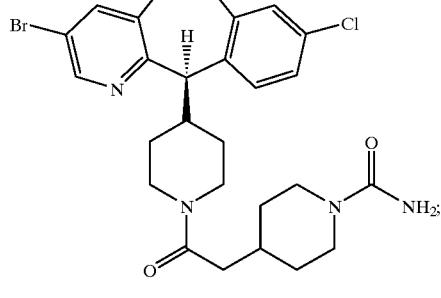
(50.0)
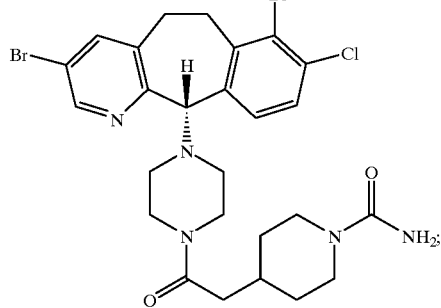
(51.0)
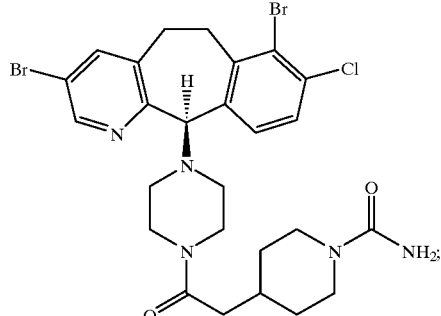

(52.0)
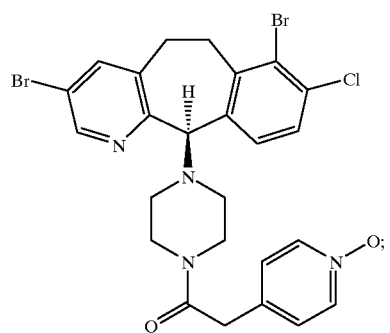
(53.0)
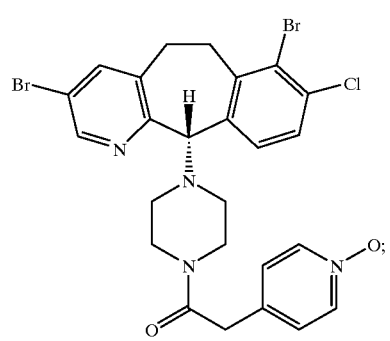
(54.0)
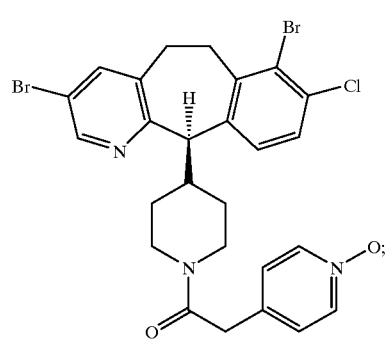
(55.0)
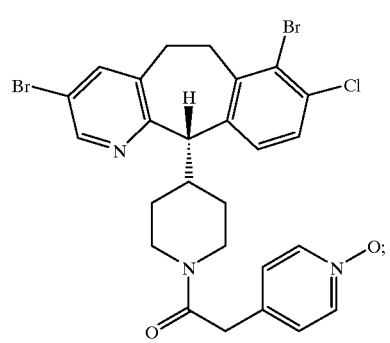
(56.0)
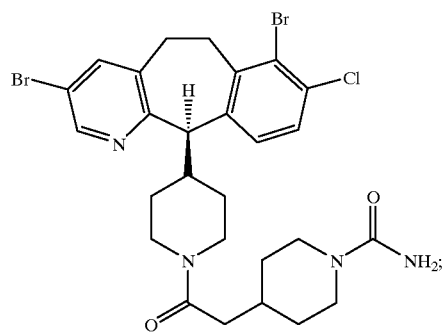
(57.0)
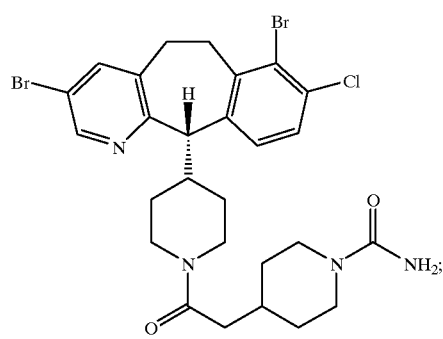
(58.0)
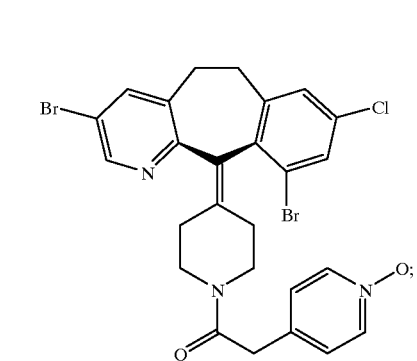
(59.0)
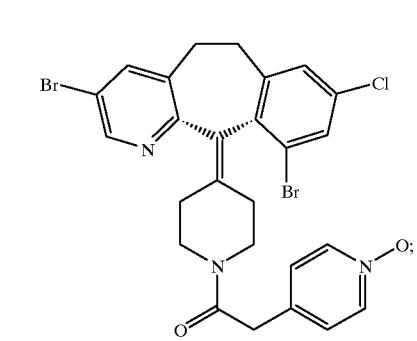

(60.0)
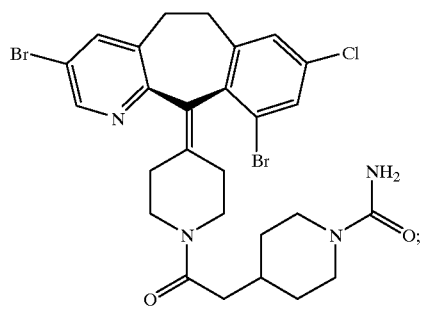
(61.0)
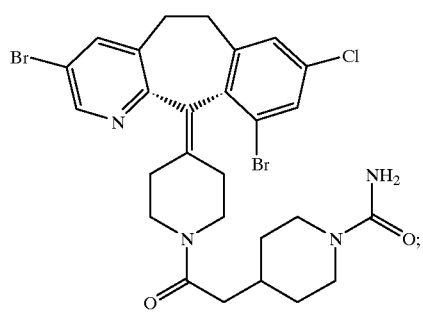
(62.0)
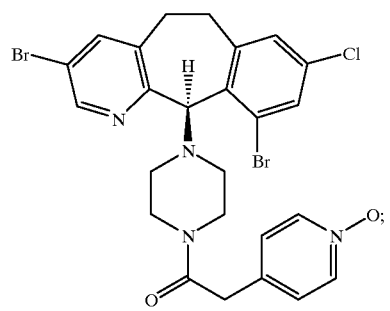
(63.0)
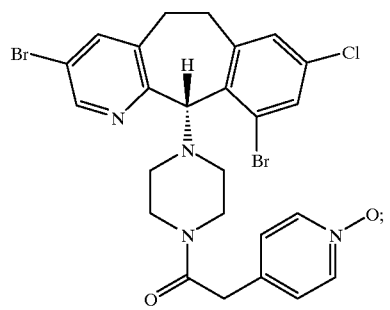
(64.0)
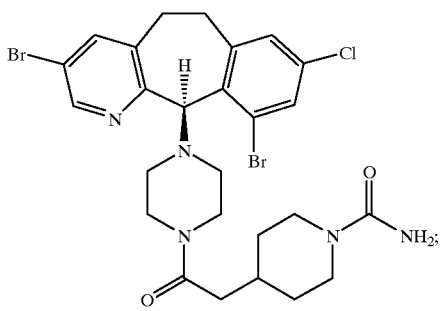
(65.0)
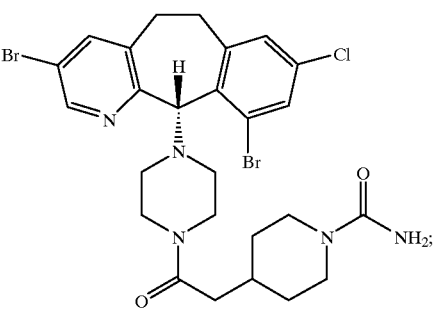
(66.0)
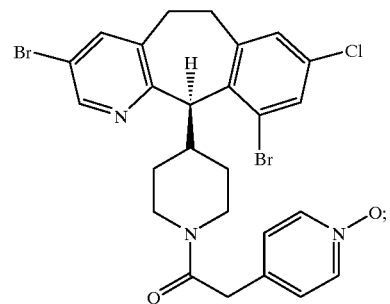
(67.0)
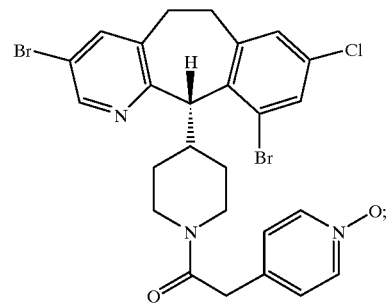
(68.0)
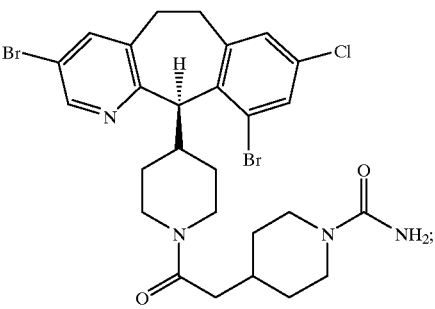
(69.0)
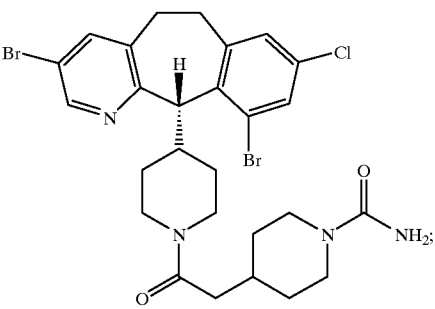

-continued
(70.0)
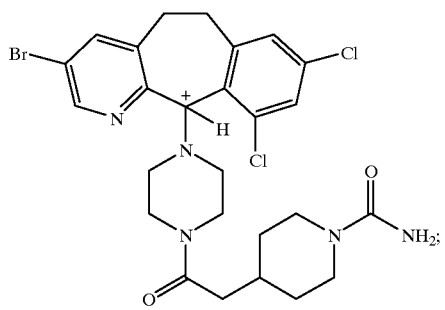
(71.0)
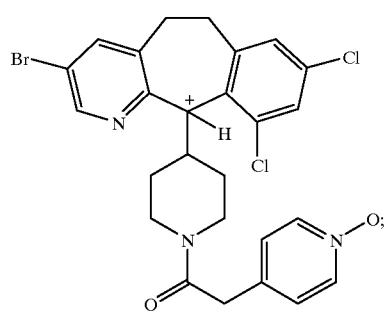
(72.0)
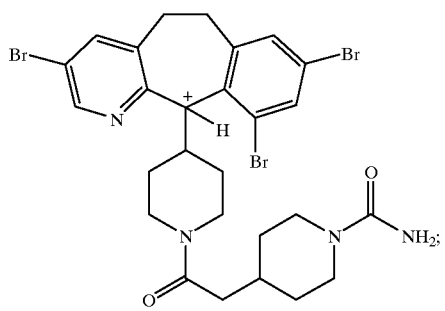
(73.0)
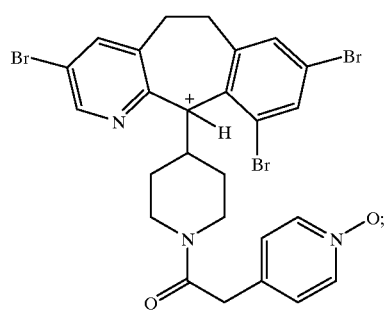
(74.0)
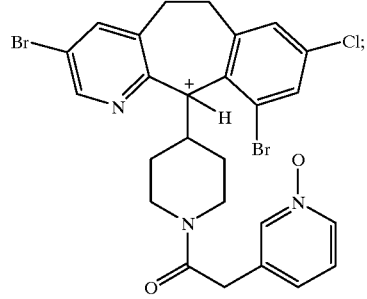
-continued
(75.0)
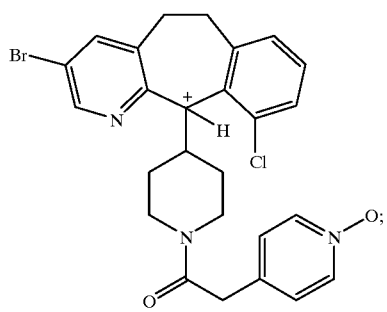
(76.0)
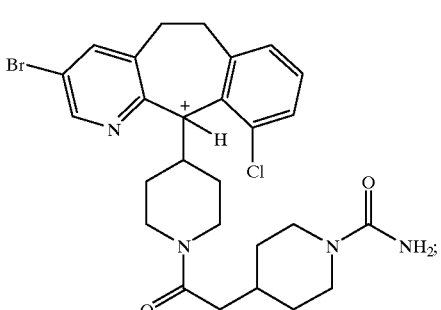
(77.0)
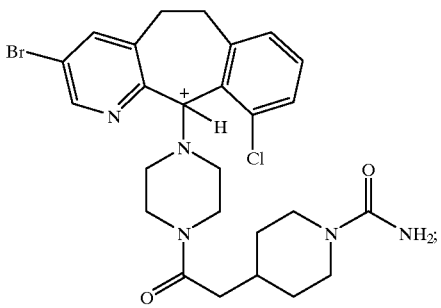
(78.0)
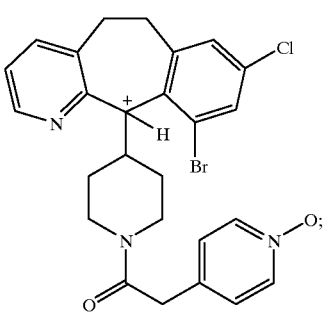

(79.0)

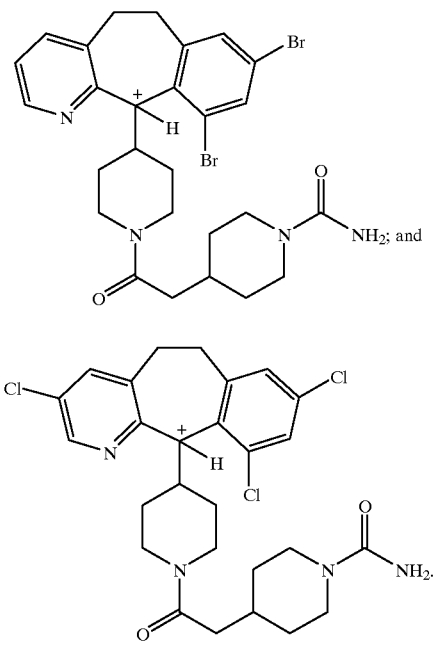

(80.0)

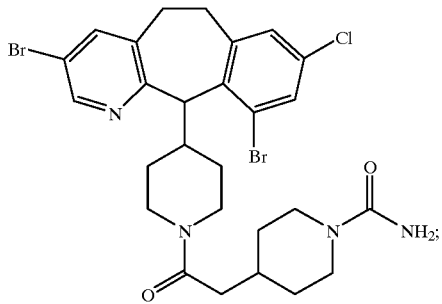

or pharmaceutically acceptable salts thereof.

A preferred compound for use as an FPT inhibitor in the method of the present invention has the formula:

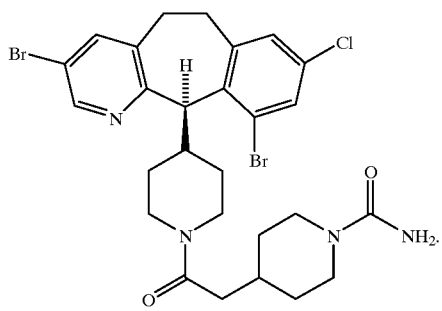

i.e., the compound 4-[2-[4-[(8-chloro-3,10-dibromo-6,11-dihydro-5H-benzo[5,6]cyclohepta[1,2-b]pyridin- 11-yl)-1-piperidinyl]-2-oxoethyl]-1-piperidinecarboxamide, preferably the (+)-isomer thereof, which has the structure See also U.S. Pat. No. 5,719,148 (issued Feb. 17, 1998) and U.S. Pat. No. 5,874,442 (issued Feb. 23, 1999), which are each expressly incorporated herein by reference.

U.S. Patent Application U.S. Ser. No. 09/216,398, expressly incorporated herein by reference, discloses compounds useful for the inhibition of FPT represented by the formula:

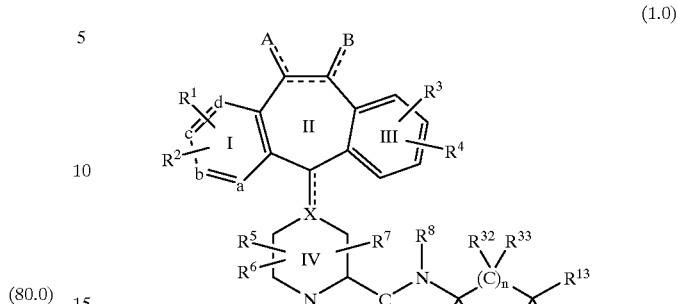

(1.0)

or a pharmaceutically acceptable salt or solvate thererof, wherein:

one of a, b, c and d represents N or $N^+O^-$, and the remaining a, b, c and d groups represent $CR^1$ or $CR^2$; or each of a, b, c, and d are independently selected from $CR^1$ or $CR^2$;

X represents N or CH when the optional bond (represented by the dotted line) is absent, and represents C when the optional bond is present;

the dotted line between carbon atoms 5 and 6 represents an optional bond, such that when a double bond is present, A and B independently represent $—R^{15}$, halo, $—OR^{16}$, $—OCO_2R^{16}$ or $—OC(O)R^{15}$, and when no double bond is present between carbon atoms 5 and 6, A and B each independently represent $H_2$, $—(OR^{16})_2$, H and halo, dihalo, alkyl and H, (alkyl)$_2$, $—H$ and $—OC(O)R^{15}$, H and $—OR^{15}$, $=O$, aryl and H, $=NOR^{15}$ or $—O—(CH_2)_p—O—$ wherein p is 2, 3 or 4;

each $R^1$ and each $R^2$ is independently selected from H, halo, $—CF_3$, $—OR^{15}$ (e.g., $—OCH_3$), $—COR^{15}$, $—SR^{15}$ (e.g., $—SCH_3$ and $—SCH_2C_6H_5$), $—S(O)_tR^{16}$ (wherein t is 0, 1 or 2, e.g., $—SOCH_3$ and $—SO_2CH_3$), $—N(R^{15})_2$, $—NO_2$, $—OC(O)R^{15}$, $—CO_2R^{15}$, $—OCO_2R^{16}$, $—CN$, $—NR^{15}COOR^{16}$, $—SR^{16}C(O)OR^{16}$ (e.g., $—SCH_2CO_2CH_3$), $—SR^{16}N(R^{17})_2$ wherein each $R^{17}$ is independently selected from H and $—C(O)OR^{16}$ provided that $R^{16}$ is not $—CH_2—$ (e.g., $—S(CH_2)_2NHC(O)O—$t-butyl and $—S(CH_2)_2NH_2$), benzotriazol-1-yloxy, tetrazol-5-ylthio, or substituted tetrazol-5-ylthio (e.g., alkyl substituted tetrazol-5-ylthio such as 1-methyl-tetrazol-5-ylthio), alkynyl, alkenyl or alkyl, said alkyl or alkenyl group optionally being substituted with halo, $—OR^{15}$ or $—CO_2R^{15}$;

$R^3$ and $R^4$ are the same or different and each independently represents H, any of the substituents of $R^1$ and $R^2$, or $R^3$ and $R^4$ taken together represent a saturated or unsaturated $C_5-C_7$ fused ring to the benzene ring (Ring III);

$R^5$, $R^6$, and $R^7$ each independently represents H, $—CF_3$, $—COR^{15}$, alkyl or aryl, said alkyl or aryl optionally being substituted with $—OR^{15}$, $—SR^{15}$, $—S(O)_tR^{16}$, $—NR^{15}COOR^{16}$, $—N(R^{15})_2$, $—NO_2$, $—COR^{15}$, $—OCOR^{15}$, $—OCO_2R^{16}$, $—CO_2R^{15}$, $OPO_3R^{15}$, or $R^5$ is combined with $R^6$ to represent $=O$ or $=S$;

$R^8$ is selected from: H, $C_3$ to $C_4$ alkyl (preferably branched chain alkyl, and most preferably $C_4$ to $C_7$ branched chain alkyl), aryl, arylalkyl, heteroaryl, heteroarylalkyl, cycloalkyl, cycloalkylalkyl, substituted alkyl, substituted aryl, substituted arylalkyl, substituted heteroaryl, substituted heteroarylalkyl, substituted cycloalkyl, substituted cycloalkylalkyl;

the substutuents for the $R^8$ substituted groups being selected from: alkyl, aryl, arylalkyl, cycloalkyl, —$N(R^{18})_2$, —$OR^{18}$, cycloalkyalkyl, halo, CN, —$C(O)N(R^{18})_2$, —$SO_2N(R^{18})_2$ or —$CO_2R^{18}$; provided that the —$OR^{18}$ and —$N(R^{18})_2$ substituents are not bound to the carbon that is bound to the N of the —C(O)NR$^8$—moiety;

each $R^{18}$ is independently selected from: H, alkyl, aryl, arylalkyl, heteroaryl or cycloalkyl;

$R^9$ and $R^{10}$ are independently selected from: H, alkyl, aryl, arylalkyl, heteroaryl, heteroarylalkyl, cycloalkyl or —$CON(R^{18})_2$ (wherein $R^{18}$ is as defined above); and the substitutable $R^9$ and $R^{10}$ groups are optionally substituted with one or more (e.g., 1–3) substituents selected from: alkyl (e.g., methyl, ethyl, isopropyl, and the like), cycloalkyl, arylalkyl, or heterarylalkyl (i.e., the $R^9$ and/or $R^{10}$ groups can be unsubstituted or can be substituted with 1–3 of the substituents described above, except when $R^9$ and/or $R^{10}$ is H); or $R^9$ and $R^{10}$ together with the carbon atom to which they are bound, form a $C_3$ to $C_6$ cycloalkyl ring;

$R^{11}$ and $R^{12}$ are independently selected from: H, alkyl, aryl, arylalkyl, heteroaryl, heteroarylalkyl, cycloalkyl, —$CON(R^{18})_2$ —$OR^{18}$ or —$N(R^{18})_2$; wherein $R^{18}$ is as defined above; provided that the —$OR^{18}$ and —$N(R^{18})_2$ groups are not bound to a carbon atom that is adjacent to a nitrogen atom; and wherein said substitutable $R^{11}$ and $R^{12}$ groups are optionally substituted with one or more (e.g., 1–3) substituents selected from: alkyl (e.g., methyl, ethyl, isopropyl, and the like), cycloalkyl, arylalkyl, or heterarylalkyl; or $R^{11}$ and $R^{12}$ together with the carbon atom to which they are bound, form a $C_3$ to $C_6$ cycloalkyl ring;

$R^{13}$ is an imidazolyl ring selected from:

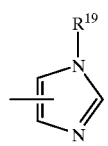

(2.0)

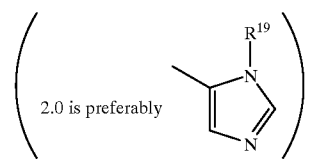

(2.1)

2.0 is preferably

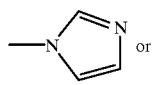

(4.0)

or

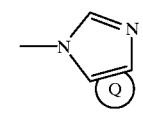

(4.1)

wherein $R^{19}$ is selected from: (1) H, (2) alkyl, (3) alkyl, (4) aryl, (5) arylalkyl, (6) substituted arylalkyl wherein the substituents are selected from halo (e.g., F and Cl) or CN, (7) —C(aryl)$_3$ (e.g., —C(phenyl)$_3$, i.e., trityl) or (8) cycloalkyl;

said imidazolyl ring 2.0 or 2.1 optionally being substituted with one or two substituents and said imidazole ring 4.0 optionally being substituted with 1–3 substituents and said imidazole ring 4.1 being optionally substituted with one substituent wherein said optional substituents for rings 2.0, 2.1, 4.0 and 4.1 are bound to the carbon atoms of said imidazole rings and are independently selected from: —NHC(O)$R^{18}$, —$C(R^{34})_2OR^{35}$, —$OR^{18}$, —$SR^{18}$, F, Cl, Br, alkyl, aryl, arylalkyl, cycloalkyl, or —$N(R^{18})_2$; $R^{18}$ is as defined above; each $R^{34}$ is independently selected from H or alkyl (preferably —$CH_3$), preferably H; $R^{35}$ is selected from H, —$C(O)OR^{20}$, or —$C(O)NHR^{20}$, and $R^{20}$ is as defined below (preferably $R^{20}$ is alkyl or cycloalkyl, most preferably cyclopentyl or cyclohexyl); Q represents an aryl ring (e.g., phenyl), a cycloalkyl ring (e.g., cyclopentyl or cyclohexyl) or a heteroaryl ring (e.g., furanyl, pyrrolyl, thienyl, oxazolyl or thiazolyl); (examples of the —$C(R^{34})_2OR^{35}$ group include —$CH_2OH$, —$CH_2OC(O)OR^{20}$ and —$CH_2OC(O)NHR^{20}$);

$R^{14}$ is selected from:

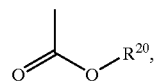

(5.0)

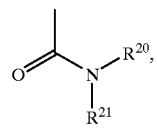

(6.0)

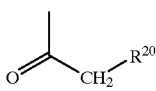

(7.0)

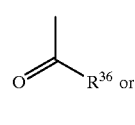

(7.1)

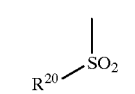

(8.0)

$R^{15}$ is selected from: H, alkyl, aryl or arylalkyl;

$R^{16}$ is selected from: alkyl or aryl;

$R^{20}$ is selected from: H, alkyl, alkoxy, aryl, arylalkyl, cycloalkyl, heteroaryl, heteroarylalkyl or heterocycloalkyl, provided that $R^{20}$ is not H when $R^{14}$ is group 5.0 or 8.0;

when $R^{20}$ is other than H, then said $R^{20}$ group is optionally substituted with one or more (e.g., 1–3) substituents selected from: halo, alkyl, aryl, —$OR^{18}$ or —$N(R^{18})_2$, wherein each $R^{18}$ group is the same or different, and wherein $R^{18}$ is as defined above, provided that said optional substituent is not bound to a carbon atom that is adjacent to an oxygen or nitrogen atom;

$R^{21}$ is selected from: H, alkyl, aryl, arylalkyl, cycloalkyl, heteroaryl, heteroarylalkyl or heterocycloalkyl;

when $R^{21}$ is other than H, then said $R^{21}$ group is optionally substituted with one or more (e.g., 1–3) substituents selected from: halo, alkyl, aryl, —OR$^{18}$ or —N(R$^{18}$)$_2$, wherein each R$^{18}$ group is the same or different, and wherein R$^{18}$ is as defined above, provided that said optional substituent is not bound to a carbon atom that is adjacent to an oxygen or nitrogen atom; n is 0–5;

each R$^{32}$ and R$^{33}$ for each n (i.e., for each —C(R$^{32}$)(R$^{33}$)—group), are independently selected from: H, alkyl, aryl, arylalkyl, heteroaryl, heteroarylalkyl, cycloalkyl, —CON(R$^{18}$)$_2$, —OR$^{18}$ or —N(R$^{18}$)$_2$; wherein R$^{18}$ is as defined above; and wherein said substitutable R$^{32}$ and R$^{33}$ groups are optionally substituted with one or more (e.g., 1–3) substituents selected from: alkyl (e.g., methyl, ethyl, isopropyl, and the like), cycloalkyl, arylalkyl, or heterarylalkyl; or R$^{32}$ and R$^{33}$ together with the carbon atom to which they are bound, form a C$_3$ to C$_6$ cycloalkyl ring; and R$^{36}$ is selected from cycloalkyl, heterocycloalkyl, or aryl (e.g., phenyl); and provided that:
(1) when R$^{14}$ is selected from: group 6.0, 7.0, 7.1 or 8.0, and X is N, then R$^8$ is selected from: C$_3$ to C$_{10}$ alkyl, substituted C$_3$ to C$_{10}$ alkyl, arylalkyl, substituted arylalkyl, heteroarylalkyl, substituted heteroarylalkyl, cycloalkylalkyl, or substituted cycloalkylalkyl;
(2) when R$^{14}$ is selected from: group 6.0, 7.0, 7.1 or 8.0, and X is N, and R$^8$ is H, then the alkyl chain between R$^{13}$ (i.e., imidazole ring 2.0, 4.0 or 4.1) and the amide moiety (i.e., the —C(O)NR$^{18}$ group) is substituted, i.e.,: (a) at least one of R$^9$, R$^{10}$, R$^{11}$, R$^{12}$, R$^{32}$, or R$^{33}$ is other than H, and/or (b) R$^9$ and R$^{10}$, and/or R$^{11}$ and R$^{12}$, are taken together to form a cycloalkyl ring;
(3) when R$^{14}$ is group 5.0, and X is N, and R$^8$ is H, then the alkyl chain between R$^{13}$ (i.e., imidazole ring 2.0, 4.0 or 4.1) and the amide moiety (i.e., the —C(O)NR$^{18}$ group) is substituted, i.e.,: (a) at least one of R$^9$, R$^{10}$, R$^{11}$, R$^{12}$, R$^{32}$, or R$^{33}$ is other than H, and/or (b) R$^9$ and R$^{10}$, and/or R$^{11}$ and R$^{12}$, are taken together to form a cyloalkyl ring.

Preferred FPT inhibitors include peptides and peptidomimetic compounds and fused-ring tricyclic compounds of the above documents (which have already been incorporated herein by reference thereto). More preferred are the fused-ring tricyclic compounds, and most preferred are the compounds of WO 97/23478.

The FPT inhibition and anti-tumor activity of the compounds used as FPT inhibitors in this invention can be determined by methods known in the art—see, for example, the in vitro Enzyme Assays, Cell-Based Assays, Cell Mat Assays, and in vivo Anti-Tumor Studies in WO 95/10516 published Apr. 20, 1995, and the soft agar assay in WO 97/23478 published Jul. 3, 1997.

USE OF CHEMOTHERAPY AND/OR RADIATION THERAPY AS ADDITIONAL AGENTS IN THE TREATMENTS OF THE PRESENT INVENTION

Chemotherapeutic agents and/or radiation can optionally be added to treatment regimens of the present invention (in addition to the combination of (1) a farnesyl protein transferase (FPT) inhibitor, and (2) an additional Ras pathway signaling inhibitor). For use of chemotherapy and/or radiation therapy in combination with only an FPT inhibitor, reference can be made to Liu, M., et al. Cancer Res. 58:4947–4956 (1998) and U.S. patent application Ser. No. 09/217,335, expressly incorporated herein by reference.

Classes of compounds that can be used as the chemotherapeutic agent include: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (paclitaxel is commercially available as Taxol®), Mithramycin, Deoxycoformycin, Mitomycin-C, L-Asparaginase, Interferons (especially IFN-α), Etoposide, and Teniposide.

Hormones and steroids (including synthetic analogs): 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645–1742, USA); the disclosure of which is incorporated herein by reference thereto.

EXAMPLES

The examples provided below describe the effect of the combination of an FPT inhibitor (SCH 66336) with a MEK inhibitor (either PD098059 or U0126) on programmed cell death (apoptosis) in H-Ras-transformed Rat2 cells. Similar to tumor cell lines, these cells exhibit a fully transformed phenotype including the ability to grow anchorage-independently in soft agar and as xenografts in nude mice.

The FPT inhibitory compound used in the following examples (SCH 66336, Schering-Plough Research Institute) has the following formula:

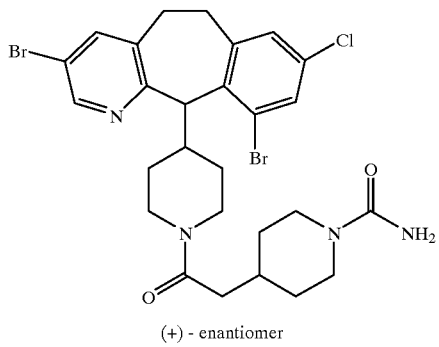

(+) - enantiomer

"PD 098059", a particular MEK inhibitor, has the following chemical structure:

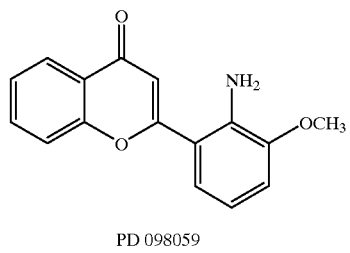

PD 098059

PD 098059 is described in more detail in Dudley et al, 1995. The Dudley et al. reference mentions that the lyophilized solid must be reconstituted into DMSO for the reagent concentrations used in the experiments described here.

"U0126", another example of a MEK inhibitor, has the flowing chemical structure:

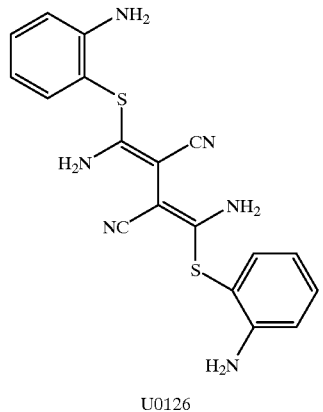

U0126

U0126 is described in more detail in Favata et al., 1998. The Favata et al. reference also mentions that the lyophilized solid must be reconstituted into DMSO for the reagent concentrations used in the experiments described here.

Materials and Methods

Cell Lines and Treatments.

In all cases the Ras sequences contained a Gly[12] to Val activating mutation. H-ras (G12V;CVLL) represents a Ser[189] to Leu mutation which generates a geranylgeranlyated form of the H-ras protein. The cDNAs representing these H-ras proteins were subcloned into the pMV7 plasmid for the generation of stable Ras expressing-Rat2 cell lines by retroviral transduction and selection with the neomycin gene (Kirschmeier et al., 1988). The stable cell lines presented here represent individual clones of Ras-expressing, neomycin-selected cells. H-ras (G12V)/Rat2, H-ras (G12V;CVLL)/Rat2, and parental Rat2 cells were propogated in DMEM containing 10% fetal calf serum, penicillum, streptomycin, non-essential amino acids, L-glutamine, and for the Ras-transformants, 200 µg/ml Geneticin (Gibco/BRL; Gaithersburg, Md.). All ras transformed cells demonstrated a fully transformed phenotype including anchorage-independent growth and tumorgenic capabilities.

PD098059 (A385-023-M005; Alexis Corporation; San Diego, Calif.) and U0126 (#V1121; Promega Corporation; Madison, Wis.) and were used according to Dudley et al. (1995) and Favata et al. (1998).

FACS Analysis.

FACS analysis was performed using standard protocols. The cells were harvested by trypsin/EDTA treatment, the trypsin was neutralized with DMEM containing 10% FCS, and the cells were pelleted at 500×g for 5 min. The cells were washed with PBS, pelleted, resuspended in 0.5 ml PBS, and fixed with 2 ml ice cold acetone:methanol (1:1) for 30 min at −20° C. To label chromosomal DNA with propidium iodide (PI), the fixed cells were washed twice with PBS prior to resuspending at 1×10⁶ cells/ml in PBS, 75 µg/ml of PI (Calbiochem; La Jolla, Calif.), 500 µg/ml RNase (Sigma; St. Louis, Mo.), for a 30 min incubation at RT. The cells were filtered through a 35 µm strainer cap (Becton Dickinson; Franklin Lakes, N.J.) and stored at 4° C. prior to FACS analysis on a FACS-Calibur (Becton Dickinson; Mountain View, Calif.). Quantification was performed using CellQuest (Becton Dickinson; Mountain View, Calif.).

Caspase Activity Assay.

H-ras transformed Rat2 and parental Rat2 cells were treated with 20 µM PD098059, 0.5 µM SCH 66336 or a combination of the two drugs for 36 h at 37βC. The cells were harvested by trypsin/EDTA, pelleted at 500×g for 5 min, washed with PBS, and repelleted. The cells were resuspended/lysed in a lysis buffer (ApoAlert CPP32/Caspase-3 Assay Kit; Clontech laboratories; Palo Alto, Calif.) containing "Complete" protease inhibitors (Boehringer Mannheim; Germany), incubated for 10 min on ice and centrifuged for 3 min at 12,000 rpm at 4° C. as recommended in the Clontech protocol. The protein concentration of the cell lysates was determined using the BCA protein assay (Pierce; Rockford, Ill.) and approximately 30 µg of each lysate assayed for Caspase-3 activity by fluorometry (CytoFluor plate reader; Perseptive Biosystems; Framingham, Mass.) using a fluorogenic peptide substrate (Ac-DEVD-AFC; Clontech; Palo Alto, Calif.).

Western Blot Analysis of ERK1,2 Phosphorylation Status.

Cells were lysed in a detergent buffer (provided with the ApoAlert CPP32/Caspase-3 Assay Kit; Clonetech; Palo Alto, Calif.) and centrifuged at 14,000 rpm for 15 min at 4° C. to pellet the cellular debris. Protein concentration of the resulting supernatant was determined by BCA protein assay (Pierce; Rockford, Ill.). Cellular proteins (20 µg) were separated on 8–16% Tris-Glycine polyacrylamide gels (Novex; San Diego, Calif.) and transferred to PVDF membranes for Western Blot analysis. The phosphorylated ERK1 and ERK2 proteins were detected using a rabbit polyclonal antibody specific for the phosphorylated form of the p42/44 MAPK proteins (phospho-Thr202/Tyr204 specific; New England Biolabs, Inc.; Beverly Mass.). Total ERK1 and ERK2 proteins were detected using a rabbit polyclonal antibody specific for the p42/44 MAPK proteins (New England Biolabs, Inc.; Beverly, Mass.). A goat anti-rabbit- HRP secondary antibody (Chemicon; Temecula, Calif.) allowed visualization by enhanced chemiluminescence (SuperSignal West Pico Chemiluminescent Substrate; Pierce; Rockford, Ill.).

RESULTS

1. Effects on Apoptosis: Fluorscence-activated Cell Sorting (FACS):

Cellular apoptotic responses can be monitored in a number of ways, including analysis of chromosomal DNA fragmentation, fluorescence-activated cell sorting (FACS) of propidium iodide-stained cells, and measurement of caspase activation. To evaluate the apoptotic response to treatment with either drug, we stained the chromosomal DNA of treated cells with propidium iodide and analyzed the individual cells by FACS. Typical cell culture populations display a large peak of cells in the G1/G0 phase of the cell cycle, with a smaller peak representing G2/M phase cells. Between these 2 peaks are cells in the S phase of the cell cycle. Cells which exhibit DNA labeling which is before the G 1/G0 peak represent cells with fragmented DNA comprising less than the diploid amount of chromosomal DNA, and thus, undergoing cell death (Dengler, et al., 1995). This measurement gives a relative quantification of apoptosis that is comparable to other apoptosis assays including TdT-mediated dUTP nick-end labeling (TUNEL analysis); Gorczyca et al., (1993) Cancer Res. 53: 1945–51. In the experiments below, we determined the percent of the total cell population in the subG0/G1 peak as a measure of percent apoptosis.

Treatment of H-Ras-transformed Rat2 cells with PD098059 alone for 36 hours resulted in a dose-dependent increase in the percent of apoptotic cells (FIG. 2). At a concentration of 20 $\mu$M PD098059, 50% of the cells were apoptotic. When the PD098059 dose-response was repeated in the presence of 100 nM SCH 66336 a very different result was observed. In the presence of 100 nM SCH 66336 alone, 30% of the cells were apoptotic. When treated with the combination, over 60% of the cells were driven into apoptosis using as little as 2.5 $\mu$M PD098059. The concentration of PD098059 required to achieve 50% apoptosis was 20 $\mu$M when this compound was used alone, but was $\leq$1 $\mu$M when used in combination with the FPT inhibitor. This indicates that SCH 66336 significantly sensitizes cells to the proapoptotic effects of PD098059.

The converse experiment was also performed. Treatment with SCH 66336 alone for 36 hours induced a dose-dependent apoptotic response (FIG. 3). Using 0.75 $\mu$M SCH 66336, 70% of the cells were apoptotic. When used alone, the concentration of SCH 66336 required to induce 50% apoptosis was between 0.25–0.5 $\mu$M. The dose-response curve for SCH 66336 displayed a leftward shift in the presence of 2.5 $\mu$M PD098059 signifying an enhanced apoptotic response. When PD098059 was present, the concentration of SCH 66336 required to induce 50% apoptosis was 50 nM.

A similar set of experiments were performed with a structurally distinct MEK inhibitor, U0126 (FIG. 4). Similar to PD098059, U0126 is a very selective inhibitor of the MEK1,2 proteins exhibiting a potent inhibition of their kinase acitivity (Farata, et al. 1990). Treatment with U0126 alone resulted in a dose-dependent induction of apoptosis in H-Ras-transformed Rat2 cells with 17% apoptotic cells observed using a concentration of 10 MM. When this experiment was repeated in the presence of 0.5 $\mu$M SCH 66336 (a concentration which induced 14% apoptosis on its own), a greater than additive response was observed with the combination. The combination of 10 $\mu$M U0126 and 0.5 $\mu$M SCH 66336 resulted in over 50% of the cells being apoptotic.

These data demonstrate a significant increase in the proapoptotic potency in H-Ras-transformed Rat2 cells of MEK inhibitors and SCH 66336 when tested in combination. In contrast to these results, untransformed parental Rat2 cells or Rat2 cells transformed with activated Ki-Ras were insensitive to apoptosis induced by either drug alone or by the combination of SCH 66336 and PD098059 (data not shown). Lack of effect in the Ki-Ras-transformed Rat2 cells may be explained, in part, by recent observations that some Ras isoforms (Ki-Ras and N-Ras) are alternatively prenylated by geranylgeranyl transferase 1 both in vitro and in cells treated with FPT inhibitors (Zhang et al., 1997; Whyte et al., 1997).

2. Effects on apoptosis: Caspase Activation: Caspases are an evolutionarily conserved family of enzymes which proteolytically degrade and dissemble the cell in response to proapoptotic signals (reviewed in Thornberry and Lazebnik, 1998). To evaluate apoptosis using this distinct biochemical end-point, we measured caspase activity in cell lysates prepared from H-Ras-transformed Rat2 cells using a fluorometric assay for caspase 3 activity (Apo-Alert CPP32/Caspase-3 Assay; Clontech). Treatment of the H-Ras-transformed cells for 24 hr with either 0.5 $\mu$M SCH 66336 or 20 $\mu$M PD098059 alone increased caspase activity above the background level of untreated cells (FIG. 5). These results are consistent with the proapoptotic effects of either drug observed by FACS analysis (FIG. 2 at 36 hr). When H-Ras-transformed Rat2 cells were treated with the combination of both drugs a greater than additive caspase-3 response was observed, again confirming the FACS results.

Little or no caspase activation was observed in the parental Rat2 cells when treated with either single agent or a combination of both drugs (FIG. 5).

3. Effects on MAPK Phosphorylation:

We investigated the ability of the FPT inhibitor SCH 66336 and the MEK inhibitor PD098059 to block MEK activation in H-ras-transformed Rat2 cells by measuring the phosphorylation state of its substrates ERK1 and ERK2 (44 and 42 Kd, respectively). Treatment of cells with 20 $\mu$M PD098059 decreased phosphorylation of both proteins (FIG. 6). Maximal inhibition was observed at the first time-point examined (6 hours) and phosphorylation remained suppressed throughout the 36 hour time-course. Treatment of cells with 0.5 $\mu$M SCH 66336 decreased phosphorylation of both proteins in a time-(FIG. 6) and dose-dependent manner (data not shown), with 0.5 $\mu$M SCH 66336 exhibiting maximal inhibition between 24–36 hours of treatment. In both cases, inhibition of phosphorylation was more profound for the 44 kDa ERK1 protein. While their phosphorylation status was decreased, the total amount of these proteins was largely unaffected by drug treatment (FIG. 6, bottom panels).

Discussion

FPT inhibitors such as SCH 66336 and MEK inhibitors such as PD098059 or U0 126 target distinct steps in a common signal transduction pathway. Surprisingly, when both agents are combined, they have a greater than additive effect on apoptosis in H-Ras-transformed Rat2 cells as measured either by FACS analysis of the subG0/G1 population or by caspase activation. Without being bound to a particular theory, there are two potential explanations for this observation. First, it is possible that this combination results in a more complete or longer-lasting (sustained) inhibition of the linear pathway outlined in FIG. 1. Alternatively, the combination efficacy may be accounted for by the fact that intracellular signaling pathways are considerably more complex and interconnected than the pathway depicted in FIG. 1. A more complex wiring diagram is shown in FIG. 7. As mentioned previously, it is clear that these pathways branch at several steps along the pathway. Growth factor receptors activate several signaling pathways via SH2-mediated interactions. Similarly, multiple Ras effectors have been identified utilizing yeast 2-hybrid and other biochemical approaches. The combined efficacy of an FPT inhibitor and a MEK inhibitor may be accounted for by their effects on distinct branches of these pathways. For example, in addition to blocking H-Ras-mediated activation of MEK, FPT inhibitors also block other Ras-effector pathways (e.g. the P13K and Rho pathways). Similarly, there is evidence for Ras-independent activation of the MEK/MAPK pathway (Duckworth and Cantley, 1997; Morrison and Cutler, 1997). While the molecular components of this Ras-independent pathway remain to be fully delineated, this suggests that an FPT inhibitor alone may not shut-down all pathways leading to MEK/MAPK activation. Therefore, the combination of these 2 classes of inhibitors may result in a more complete blockade.

Regardless of the mechanism, the ex vivo data with the combination of SCH 66336 and PD098059 demonstrates a striking potentiation of apoptosis-inducing activity. Furthermore, this type of enhanced efficacy in combination is extendable to include other agents that target signal transduction pathways, (e.g., agents which block growth factor receptors). As stated above, such effects may result from (i) a more complete inhibition of the growth factor—Ras signaling pathway than that achieved with single agent treatment; or (ii) simultaneous inhibition of multiple signaling pathways. For example, many tumors may be driven by the action of multiple growth factors each acting in an autocrine or paracrine fashion to drive proliferation through their cognate receptors. The blockade of one of these receptor pathways using antibodies or tyrosine kinase inhibitors may exert an antitumor effect by blocking that signaling pathway, however other receptor-driven pathways will be unaffected. The addition of a FPT inhibitor may shut down signaling from these other pathways resulting in a more complete inhibition of signal transduction and, thus, exhibiting a synergistic antitumor effect. Furthermore, because growth factor receptors are known to initiate multiple signaling cascades (e.g. Ras/MEK, phospholipase Cγ, and PI3K), inhibition of the Ras pathway with a FPT inhibitor or a MEK inhibitor may have no effect on the signaling capacity of these other pathways. Thus, the addition of a growth factor receptor antibody o r tyrosine kinase inhibitor to a tumor cell treated with a FPT inhibitor may result in a more complete inhibition of signaling and have a synergistic antitumor effect by shutting down those pathways which are unaffected by the FPT inhibitor.

Similar types of synergy may also be observed by combining FPT inhibitors with agents that target other steps in these signaling pathways (e.g. Raf inhibitors, SH2 inhibitors, PI3K inhibitors, etc.).

PHARMACEUTICAL COMPOSITIONS

Inert, pharmaceutically acceptable carriers used for preparing pharmaceutical compositions of the FPT inhibitors and the Ras signaling pathway inhibitors described herein can be solid or liquid. Solid preparations include powders, tablets, dispersible granules, capsules, cachets and suppositories. The powders and tablets may comprise from about 5 to about 70% active ingredient. Suitable solid carriers are known in the art, e.g., magnesium carbonate, magnesium stearate, talc, sugar, and/or lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into conveniently sized molds, allowed to cool and thereby solidify.

Liquid preparations include solutions, suspensions and emulsions. As an example may be mentioned water or water-propylene glycol solutions for parenteral injection. Liquid preparations may also include solutions for intranasal administration.

Aerosol preparations suitable for inhalation may include solutions and solids in powder form, which may be in combination with a pharmaceutically acceptable carrier, such as an inert compressed gas.

Also included are solid preparations which are intended for conversion, shortly before use, to liquid preparations for either oral or parenteral administration. Such liquid forms include solutions, suspensions and emulsions.

The FPT inhibitors and the additional Ras pathway inhibitors described herein may also be deliverable transdermally. The transdermal compositions can take the form of creams, lotions, aerosols and/or emulsions and can be included in a transdermal patch of the matrix or reservoir type as are conventional in the art for this purpose.

Preferably the compounds are administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.5 mg to 1000 mg, preferably from about 1 mg to 300 mg, more preferably 5 mg to 200 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The amount and frequency of administration of the FPT inhibitors and the additional Ras pathway inhibitors will be regulated according to the judgment of the attending clinician (physician) considering such factors as age, condition and size of the patient as well as severity of the disease being treated. In general, dosage for an FPT inhibitor (when used as a single agent) can conceivably have an upper range of 2000 mg/day, preferably in a range of from 50 to 400 mg/day in cases where the FPT inhibitor is a fused-ring tricyclic benzocycloheptapyridine. However, in the combination therapy of the present invention, a preferred low dosage regimen of the FPT inhibitors is, e.g., oral administration of an amount in the range of from 1.4 to 400 mg/day, more preferably 1.4 to 350 mg/day, even more preferably 3.5 to 70 mg/day, preferably with a B.I.D. dosing schedule. A particularly low dosage range can be 1.4 to 70 mg/day.

The additional Ras pathway inhibitors can be administered according to therapeutic protocols well known in the art. See, e.g., Pegram, M. D., et.al. (1998). J Clin Oncol. 16:2659–2671. It will be apparent to those skilled in the art that the administration of the additional Ras pathway inhibitor can be varied depending on the disease being treated and the known effects of the additional Ras pathway inhibitor on that disease. Also, in accordance with the knowledge of the skilled clinician, the therapeutic protocols (e.g., dosage amounts and times of administration) can be varied in view of the observed effects of the administered therapeutic agents (i.e., additional Ras pathway inhibitor) on the patient, and in view of the observed responses of the disease to the administered therapeutic agents. In general, dosage for an additional Ras signaling pathway inhibitor (when used as a single agent) can be, e.g., in the range of 5 to 2000 mg/day. However, in the combination therapy of the present invention, a preferred low dosage regimen of an additional Ras signaling pathway inhibitor (e.g., a MEK inhibitor) is administration of an amount in the range of from 1 to 350 mg/day, more preferably 3.5 to 70 mg/day, preferably with a B.I.D. dosing schedule. A particularly low dosage range can be 1 to 70 mg/day.

Thus, in a preferred example of combination therapy in the treatment of cancers (e.g., pancreatic, lung or bladder cancer), the FPT inhibitor can be SCH 66336, as identified previously, administered orally in an amount of 70 mg/day, in two divided doses, on a continuous dosing regimen; and the additional Ras signaling pathway inhibitor can be PD098059 (or an analogue thereof) administered in an amount of 350 mg/day, in two divided doses, on a continuous dosing regimen.

In another preferred example of combination therapy in the treatment of cancers (e.g., pancreatic, lung or bladder cancer), the FPT inhibitor is SCH 66336, as identified previously, administered orally in an amount of 70 mg/day, in two divided doses, on a continuous dosing regimen; and the additional Ras signaling pathway inhibitor is U0126 (or an analogue thereof) administered in an amount of 350 mg/day, in two divided doses, on a continuous dosing regimen.

In the methods of this invention, an FPT inhibitor is administered concurrently or sequentially with an additional Ras pathway inhibitor. Thus, it is not necessary that, for example, the additional Ras pathway inhibitor and the FPT inhibitor should be administered simultaneously or essentially simultaneously. The advantage of a simultaneous or essentially simultaneous administration is well within the determination of the skilled clinician.

Also, in general, the FPT inhibitor and the additional Ras pathway inhibitor do not have to be administered in the same pharmaceutical composition, and may, because of different physical and chemical characteristics, have to be administered by different routes. For example, the FPT inhibitor may be administered orally to generate and maintain good blood levels thereof, while the additional Ras pathway inhibitor may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of FPR inhibitor and additional Ras pathway inhibitor will depend upon the diagnosis of the attending physicians and their judgement of the condition of the patient and the appropriate treatment protocol.

The FPT inhibitor and additional Ras pathway inhibitor may be administered concurrently (e.g., simultaneously, essentially simultaneously or within the same treatment protocol) or sequentially, depending upon the nature of the proliferative disease, the condition of the patient, and the actual choice of the additional Ras pathway inhibitor to be administered in conjunction (i.e., within a single treatment protocol) with the FPT inhibitor.

If the FPT inhibitor and additional Ras pathway inhibitor are not administered simultaneously or essentially simultaneously, then the initial order of administration of the FPT inhibitor and additional Ras pathway inhibitor may not be important. Thus, the FPT inhibitor may be administered first followed by the administration of the additional Ras pathway inhibitor; or the additional Ras pathway inhibitor may be administered first followed by the administration of the FPT inhibitor. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the additional Ras pathway inhibitor may be administered first, and then the treatment continued with the administration of the FPT inhibitor followed, where determined advantageous, by the administration of the additional Ras pathway inhibitor, and so on until the treatment protocol is complete.

Thus, in accordance with experience and knowledge, the practising physician can modify each protocol for the administration of a component (therapeutic agent—i.e., FPT inhibitor, additional Ras pathway inhibitor) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., Calif.T or MRI scan, and successive measurements can be used to judge whether or not growth of the tumor has been retarded or even reversed. Relief of disease-related symptoms such as pain, and improvement in overall condition can also be used to help judge effectiveness of treatment. (Of course, as indicated previously, effective treatment using the methods of the present invention preferably results in a synergistic level of cancer cell death and/or tumor regression).

The following are examples (Examples 1–4) of capsule formulations for the FPT Inhibitory Compound:

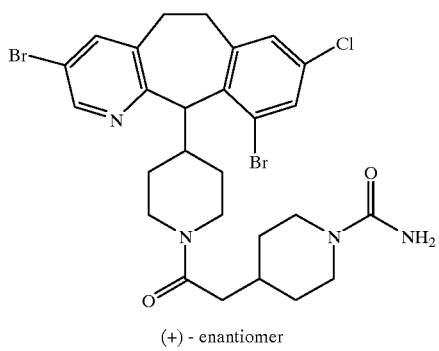

(+) - enantiomer

Examples 1 and 2

Capsule Formulation

| Composition | Example 1 mg/capsule | Example 2 mg/capsule | % Composition |
|---|---|---|---|
| Solid Solution | 100 | 400.0 | 84.2 |
| Silicon Dioxide NF[1] | 0.625 | 2.5 | 0.5 |
| Magnesium Stearate NF[2] | 0.125 | 0.5 | 0.1 |
| Croscarmellose Sodium NF | 11.000 | 44.0 | 9.3 |
| Pluronic F68 NF | 6.250 | 25.0 | 5.3 |
| Silicon Dioxide NF[3] | 0.625 | 2.5 | 0.5 |
| Magnesium Stearate NF[4] | 0.125 | 0.5 | 0.1 |
| TOTAL | 118.750 | 475.00 | |
| Capsule size | No. 4 | No. 0 | |

METHOD (Examples 1 and 2)
Preparation of Solid Solution

| Composition | g/batch | % Composition |
|---|---|---|
| FPT Inhibitory Compound | 80 | 33.3 |
| Povidone NF K29/32 | 160 | 66.6 |
| Methylene Chloride | 5000 mL | evaporates |

Crystalline FPT Inhibitory Compound and the povidone were dissolved in methylene chloride. The solution was dried using a suitable solvent spray dryer. The residue was then reduced to fine particles by grinding. The powder was then passed through a 30 mesh screen. The powder was found to be amorphous by x-ray analysis.

The solid solid solution, silicon dioxide[1] and magnesium stearatel[2] were mixed in a suitable mixer for 10 minutes. The mixture is compacted using a suitable roller compactor and milled using a suitable mill fitted with 30 mesh screen. Croscarmellose sodium, Pluronic F68 and silicon dioxide[3] are added to the milled mixture and mixed further for 10 minutes. A premix was made with magnesium stearate[4] and equal portions of the mixture. The premix was added to the remainder of the mixture and mixed for 5 minutes. the mixture was encapsulated in hard shell gelatin capsule shells.

Examples 3 and 4

Capsule Formulation

| Composition | Example 3 mg/capsule | Example 4 mg/capsule | % Composition |
|---|---|---|---|
| Solid Solution | 400 | 200.0 | 80.0 |
| Silicon Dioxide NF[1] | 3.75 | 1.875 | 0.75 |
| Magnesium Stearate NF[2] | 0.125 | 0.625 | 0.25 |
| Croscarmellose Sddium NF | 40.00 | 20.00 | 8.0 |
| Pluronic F68 NF | 50.00 | 25.00 | 10 |
| Silicon Dioxide NF[3] | 3.75 | 1.875 | 0.75 |
| Magnesium Stearate NF[4] | 1.25 | 0.625 | 0.25 |
| TOTAL | 500.00 | 250.00 | |
| Capsule size | No. 0 | No. 2 | |

METHOD (Examples 3 and 4)
Preparation of Solid Solution

| Composition | g/batch | % Composition |
|---|---|---|
| FPT Inhibitory Compound | 15 | 50 |
| Povidone NF K29/32 | 15 | 50 |
| Methylene Chloride | 140 mL | evaporates |
| Methanol | 60 mL | evaporates |

Crystalline FPT Inhibitory Compound and the povidone were dissolved in a mixture of methylene chloride and methanol. The solution was dried using a suitable solvent spray dryer. The residue was then reduced to fine particles by grinding. The powder was then passed through a 30 mesh screen. The powder was found to be amorphous by x-ray analysis.

The solid solid solution, silicon dioxide[1] and magnesium stearate[2] were mixed in a suitable mixer for 10 minutes. The mixture is compacted using a suitable roller compactor and milled using a suitable mill fitted with 30 mesh screen. Croscarmellose sodium, Pluronic F68 and silicon dioxide[3] are added to the milled mixture and mixed further for 10 minutes. A premix was made with magnesium stearate[4] and equal portions of the mixture. The premix was added to the remainder of the mixture and mixed for 5 minutes. The mixture was encapsulated in hard shell gelatin capsule shells.

For information on formulations, reference can also be made to U.S. patent application Ser. Nos. 08/997168 and 60/068387 (filed Dec. 22, 1997), expressly incorporated herein by reference.

The scope of the invention in its pharmaceutical composition aspect is not to be limited by the examples provided.

All documents (e.g., publications and patent applications) cited herein are incorporated by reference to the same extent as if each individual document was specifically and individually indicated to be incorporated by reference.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

References

Alessi, D. R., et. al. (1995). J Biol Chem. 270:27489–27494.
Barrington, R. E., et. al. (1998). Mol Cell Biol. 18:85–92.
Bishop, W. R., et. al. (1995). J Biol Chem. 270:30611–30618.
Campbell, S. L., et. al. (1998). Oncogene. 17:1395–1413.
Dengler, W. A., et. al. (1995). Anticancer Drugs. 6:522–32.
Duckworth, B. C., and Cantley, L. C. (1997). J Biol Chem. 272:27665–27670.
Dudley, D. T., et. al. (1995). Proc Natl Acad Sci USA. 92:7686–7689.
Favata, M. F., et. al. (1998). J Biol Chem. 273:18623–32.
Fry, D. W., et. al. (1994). Science. 9:1093–1095.
Goldstein, N. I., et. al. (1995). Clin Cancer Res. 1:1311–1318.
Gorczyca et. al., (1993) Cancer Res. 53: 1945–51.
Graham, N. (1995). Exp Opin Ther Patents. 5:1269–1285.
Gutkind, J. S. (1998). J Biol Chem. 273:1839–1842.
Heldin, C. H. (1995). Cell. 80:213–23.
Hung, W. C., and Chaung, L. Y. (1998). Int J Oncol. 12:137–140.
James, G. L., et. al. (1994). J Biol Chem. 269:27705–27714.
Kohl, N., et. al. (1995). Nature Medicine. 1:792.
Kovalenko, M., et. al. (1994). Cancer Res. 54:6106–6114.
Lebowitz, P. F., et. al. (1997). J Biol Chem. 272:15591–15594.
Levitzki, A., and A. Gazit. (1995). Science. 267:1782–1788.
Liu, M., et. al. (1998). Cancer Res. 58:4947–4956.
Lowy, D. R., and Willumsen, B. (1993) Annu Rev Biochem. 62:851–8091.
Mendelson, J. (1992). J National Can Inst 13:125–131.
Moasser, M. M., et. al. (1998). Proc Natl Acad Sci. 95:1369–1374.
Monia, B. P., et. al. (1996). Nucleosides and Nucleotides Their Biological Applications-1. Supp 34.
Morrison, D. K., and Cutler, R. E. (1997). Curr Opin Cell Biol. 9:174–179.
Moyer, J. D., et. al. (1997). Cancer Res. 57: 4838–4848.
Norgaard, P., et. al. (1999). Clin Cancer Res. 5:35–42.
Pegram, M. D., et. al. (1998). J Clin Oncol. 16:2659–2671.
Raff, M. (1998). Nature. 396:119–122.
Resnicoff, M. (1998). Int J Mol Med. 1:883–888.
Suzuki, N., et. al. (1998). Proc Natl Acad Sci USA. 95:15356–15361.
Thornberry, N. A. and Lazebnik, Y. (1998). Science. 281:1312–1316.
Trahey, M., and McCormick, F. (1987). Science. 238:542–5.
Wang, H. M., et. al. (1998). Anticancer Res. 18: 2297–2300.
Whyte, D. B., et. al. (1997). J Biol Chem. 272:14459–14464.
Zhang, F. L., (1997). J Biol Chem. 272:10232–10239.

What is claimed is:

1. A method of treating cancer in a patient in need of such treatment, said treatment comprising administering (1) a farnesyl protein transferase inhibiting amount of a fused-ring tricyclic benzocycloheptapyridine and (2) an additional Ras signaling pathway inhibitor, in amounts effective to induce a synergistic level of cancer cell death.

2. The method of claim 1 wherein the additional Ras signaling pathway inhibitor is a kinase inhibitor.

3. The method of claim 1 wherein the additional Ras signaling pathway inhibitor inhibits an element downstream of Ras in the Ras signaling pathway.

4. The method of claim 1 wherein the additional Ras signaling pathway inhibitor is a MEK inhibitor.

5. The method of claim 1 wherein the additional Ras signaling pathway inhibitor is a growth factor receptor inhibitor.

6. The method of claim 5 wherein the growth factor receptor inhibitor is a tyrosine kinase inhibitor.

7. The method of claim 6 wherein the tyrosine kinase inhibitor is a small molecule selected from the group consisting of (1) an erbB2 receptor inhibitor, (2) a PDGF receptor inhibitor, (3) an IGF receptor inhibitor, and (4) a EGF receptor tyrosine kinase inhibitor.

8. The method of claim 5 wherein the growth factor receptor inhibitor is an antibody directed against the extracellular domain of a growth factor receptor.

9. The method of claim 8 wherein the antibody is a monoclonal antibody which targets the erbB2 receptor or a monoclonal antibody which targets the EGF receptor.

10. The method of claim 5 wherein the growth factor receptor inhibitor is an antisense molecule directed against any of the protein components of the Ras signaling pathway.

11. The method of claim 1, wherein the fused-ring tricyclic benzocycloheptapyridine is administered in an amount of from 1.4 to 400 mg/day.

12. The method of claim 11, wherein the fused-ring tricyclic benzocycloheptapyridine is administered in an amount of from 3.5 to 70 mg/day.

13. The method of claim 1, wherein the additional Ras pathway inhibitor is administered in an amount of from 1 to 350 mg/day.

14. The method of claim 13, wherein the additional Ras pathway inhibitor is administered in an amount of from 3.5 to 70 mg/day.

15. The method of claim 1 wherein said fused-ring tricyclic benzocycloheptapyridine and said additional Ras pathway inhibitor are administered simultaneously.

16. The method of claim 1 wherein said fused-ring tricyclic benzocycloheptapyridine and said additional Ras pathway inhibitor are administered sequentially.

17. The method of claim 16 wherein said additional Ras pathway inhibitor is administered first.

18. The method of claim 16 wherein said fused-ring tricyclic benzocycloheptapyridine is administered first.

19. The method of claim 1 wherein the cancer is: lung cancer, pancreatic cancer, colon cancer, ovarian cancer, cancers of the liver, myeloid leukemia, melanoma, thyroid follicular cancer, bladder carcinoma, glioma, myelodysplastic syndrome, breast cancer or prostate cancer.

20. The method of claim 1 further comprising administering a chemotherapeutic agent.

21. The method of claim 20 wherein said chemotherapeutic agent is selected from: Uracil mustard, Chlormethine, Cyclophosphamide, Ifosfamide, Melphalan, Chlorambucil, Pipobroman, Triethylenemelamine, Triethylenethiophosphoramine, Busulfan, Carmustine, Lomustine, Streptozocin, Dacarbazine, Temozolomide, Methotrexate, 5-Fluorouracil, Floxuridine, Cytarabine, 6-Mercaptopurine, 6-Thioguanine, Fludarabine phosphate, Pentostatine, Gemcitabine, Vinblastine, Vincristine, Vindesine, Bleomycin, Dactinomycin, Daunorubicin, Doxorubicin, Epirubicin, Idarubicin, Paclitaxel, Mithramycin, Deoxycoformycin, Mitomycin-C, L-Asparaginase, Interferons, Etoposide, Teniposide 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, CPT-11, Anastrazole, Letrazole, Capecitabine, Reloxafine, Droloxafine, gemcitabine, paclitaxel, or Hexamethylmelamine.

22. The method of claim 20 wherein said antineoplastic agent is temozolomide.

23. The method of claim 1 further comprising administering radiation.

24. The method of claim 1 wherein cancer cell death occurs through apoptosis.

25. A method of treating cancer in a patient in need of such treatment, said treatment comprising administering, concurrently or sequentially, an effective amount of (1) a farnesyl protein transferase inhibitor having the formula:

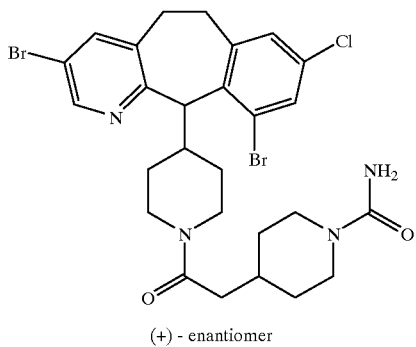

(+) - enantiomer and (2) an additional Ras signaling pathway inhibitor.

26. The method of claim 25 wherein the additional Ras signaling pathway inhibitor is a kinase inhibitor.

27. The method of claim 25 wherein the additional Ras signaling pathway inhibitor inhibits an element downstream of Ras in the Ras signaling pathway.

28. The method of claim 25 wherein the additional Ras pathway inhibitor is a MEK inhibitor.

29. The method of claim 25 wherein the additional Ras pathway inhibitor is a growth factor receptor inhibitor.

30. The method of claim 29 wherein the growth factor receptor inhibitor is a tyrosine kinase inhibitor.

31. The method of claim 30 wherein the tyrosine kinase inhibitor is a small molecule selected from the group consisting of (1) an erbB2 inhibitor, (2) a PDGF receptor inhibitor, (3) an IGF receptor inhibitor, and (4) a EGF receptor tyrosine kinase inhibitor.

32. The method of claim 29 wherein the growth factor receptor inhibitor is an antibody directed against the extracellular domain of a growth factor receptor.

33. The method of claim 32 wherein the antibody is a monoclonal antibody which targets the erbB2 or a monoclonal antibody which targets the EGF receptor.

34. The method of claim 29 wherein the growth factor receptor inhibitor is an antisense molecule directed against any of the protein components of the Ras signaling pathway.

35. The method of claim 25, wherein the farnesyl protein transferase inhibitor is administered in an amount of from 1.4 to 400 mg/day.

36. The method of claim 35, wherein the farnesyl protein transferase inhibitor is administered in an amount of from 3.5 to 70 mg/day.

37. The method of claim 25, wherein the additional Ras pathway inhibitor is administered in an amount of from 1 to 350 mg/day.

38. The method of claim 37, wherein the additional Ras pathway inhibitor is administered in an amount of from 3.5 to 70 mg/day.

39. A method of inducing a synergistic level of cancer cell death in a cancer patient, comprising administering effective amounts of (1) a farnesyl protein transferase inhibiting amount of a fused-ring tricyclic benzocycloheptapyridine and (2) an additional Ras signaling pathway inhibitor.

40. The method of claim 39 wherein the additional Ras signaling pathway inhibitor is a kinase inhibitor.

41. The method of claim 39 wherein the additional Ras signaling pathway inhibitor inhibits an element downstream of Ras in the Ras signaling pathway.

42. The method of claim 39 wherein the additional Ras signaling pathway inhibitor is a MEK inhibitor.

43. The method of claim 39 wherein the additional Ras signaling pathway inhibitor is a growth factor receptor inhibitor.

44. The method of claim 43 wherein the growth factor receptor inhibitor is a tyrosine kinase inhibitor.

45. The method of claim 44 wherein the tyrosine kinase inhibitor is a small molecule selected from the group consisting of (1) an erbB2 inhibitor, (2) a PDGF receptor inhibitor, (3) an IGF receptor inhibitor, and (4) a EGF receptor tyrosine kinase inhibitor.

46. The method of claim 43 wherein the growth factor receptor inhibitor is an antibody directed against the extracellular domain of a growth factor receptor.

47. The method of claim 46 wherein the antibody is a monoclonal antibody which targets the erbB2 or a monoclonal antibody which targets the EGF receptor.

48. The method of claim 43 wherein the growth factor receptor inhibitor is an antisense molecule directed against any of the protein components of the Ras signaling pathway.

49. The method of claim 39, wherein the fused-ring tricyclic benzocycloheptapyridine is administered in an amount of from 1.4 to 400 mg/day.

50. The method of claim 49 wherein the fused-ring tricyclic benzocycloheptapyridine is administered in an amount of from 3.5 to 70 mg/day.

51. The method of claim 39, wherein the additional Ras pathway inhibitor is administered in an amount of from 1 to 350 mg/day.

52. The method of claim 51, wherein the additional Ras pathway inhibitor is administered in an amount of from 3.5 to 70 mg/day.

53. A method of treating cancer in a patient in need of such treatment, said treatment comprising administering (1) a farnesyl protein transferase inhibiting amount of a fused-ring tricyclic benzocycloheptapyridine and (2) an additional Ras signaling pathway inhibitor, wherein the fused-ring tricyclic benzocycloheptapyridine is administered in an amount of from 1.4 to 400 mg/day.

54. A method of treating cancer in a patient in need of such treatment, said treatment comprising administering (1) a farnesyl protein transferase inhibiting amount of a fused-ring tricyclic benzocycloheptapyridine and (2) an additional Ras signaling pathway inhibitor, wherein the additional Ras pathway inhibitor is administered in an amount of from 1 to 350 mg/day.

55. A method of regressing tumor volume in a cancer patient, comprising administering effective amounts of (1) a farnesyl protein transferase inhibiting amount of a fused-ring tricyclic benzocycloheptapyridine and (2) an additional Ras signaling pathway inhibitor.

* * * * *